United States Patent
Gironella Cos et al.

(10) Patent No.: US 11,104,959 B2
(45) Date of Patent: Aug. 31, 2021

(54) IN VITRO METHOD FOR IDENTIFYING PANCREATIC CANCER OR INTRADUCTAL PAPILLARY MUCINOUS NEOPLASM OF THE PANCREAS

(71) Applicants: ADVANCED MARKER DISCOVERY, S.L., Valladolid (ES); CENTRO DE INVESTIGACIÓN BIOMÉDICA EN RED, Madrid (ES); HOSPITAL CLINIC DE BARCELONA, Barcelona (ES)

(72) Inventors: Meritxel Gironella Cos, Barcelona (ES); Antoni Castells Garangou, Barcelona (ES)

(73) Assignees: Advanced Marker Discovery, S.L., Valldolid (ES); Centro de Investigación Biomedica en Red, Madrid (ES); Hospital Clinic de Barcelona, Barcelona (ES)

( * ) Notice: Subject to any disclaimer, the term of this patent is extended or adjusted under 35 U.S.C. 154(b) by 98 days.

(21) Appl. No.: 16/095,929

(22) PCT Filed: Apr. 21, 2017

(86) PCT No.: PCT/EP2017/059498
§ 371 (c)(1),
(2) Date: Oct. 23, 2018

(87) PCT Pub. No.: WO2017/186588
PCT Pub. Date: Nov. 2, 2017

(65) Prior Publication Data
US 2019/0330699 A1    Oct. 31, 2019

(30) Foreign Application Priority Data

Apr. 26, 2016  (EP) .................................... 16382182

(51) Int. Cl.
*C12Q 1/6886* (2018.01)
*C12Q 1/686* (2018.01)
*C12Q 1/6837* (2018.01)

(52) U.S. Cl.
CPC ......... *C12Q 1/6886* (2013.01); *C12Q 1/6837* (2013.01); *C12Q 1/686* (2013.01); *C12Q 2600/112* (2013.01); *C12Q 2600/158* (2013.01); *C12Q 2600/16* (2013.01); *C12Q 2600/178* (2013.01)

(58) Field of Classification Search
CPC .............................. C12Q 1/6886; C12Q 1/686
See application file for complete search history.

(56) References Cited

U.S. PATENT DOCUMENTS

| | | | |
|---|---|---|---|
| 2009/0099034 A1* | 4/2009 | Ahlquist | C12Q 1/6809 506/9 |
| 2014/0100124 A1 | 4/2014 | Wylie et al. | |
| 2016/0046988 A1* | 2/2016 | Walter | C12Q 1/6816 435/6.11 |

FOREIGN PATENT DOCUMENTS

| | | |
|---|---|---|
| EP | 2 518 158 A1 | 10/2012 |
| WO | 2012/083969 A2 | 6/2012 |
| WO | 2013/040251 A2 | 3/2013 |

OTHER PUBLICATIONS

Goedeke (A Regulatory Role for MicroRNA 33 in Controlling Lipid Metabolism Gene Expression, Mol. Cell. Biol., 33(11): 2339-2352,2013. (Year: 2013).*
Genechip, "Data Sheet GeneChip™ miRNA 3.0 Array," Mar. 29, 2012, retrieved from the internet: http://www.carrerasresearch.org/genechip-mirna-3-0-array_38713.pdf (retrieved on. Oct. 21, 2015).
International Search Report and Written Opinion of International Application No. PCT/EP2017/059498, dated Jul. 13, 2017, 17 pages.
Andrejevic-Blant et al., "Pancreatic intraductal papillary-mucinous neoplasms: a new and evolving entity," *Virchows Arch* 451:863-869, 2007.

(Continued)

*Primary Examiner* — Angela M. Bertagna
*Assistant Examiner* — Carolyn L Greene
(74) *Attorney, Agent, or Firm* — McCarter & English, LLP; Jill Ann Mello

(57) ABSTRACT

The present invention refers to an in vitro method for screening for subjects at risk of developing pancreatic cancer or intraductal papillary mucinous neoplasm of the pancreas (IPMN) comprising: (a) measuring the expression pattern or level of at least hsa-miR-33a*, or of at least hsa-miR-320a, or of at least hsa-let-7e, or of at least hsa-let-7f, or of at least hsa-miR-1257, or of at least hsa-miR-1304, or of at least hsa-miR-151b, or of at least hsa-miR-3120-3p, or of at least hsa-miR-3133, or of at least hsa-miR-3714, or of at least hsa-miR-4468, or of at least hsa-miR-4639-5p, or of at least hsa-miR-4713-5p, or of at least hsa-miR-4714-5p, or of at least hsa-miR-4770, or of at least hsa-miR-548d-3p, or of at least hsa-miR-761, obtained from an isolated biological sample of the subjects to be screened; and (b) comparing said expression pattern or level of at least hsa-miR-33a*, or of at least hsa-miR-320a, or of at least hsa-let-7e, or of at least hsa-let-7f, or of at least hsa-miR-1257, or of at least hsa-miR-1304, or of at least hsa-miR-151b, or of at least hsa-miR-3120-3p, or of at least hsa-miR-3133, or of at least hsa-miR-3714, or of at least hsa-miR-4468, or of at least hsa-miR-4639-5p, or of at least hsa-miR-4713-5p, or of at least hsa-miR-4714-5p, or of at least hsa-miR-4770, or of at least hsa-miR-548d-3p, or of at least hsa-miR-761, of the subjects to be screened with an already established expression pattern or level, wherein over expression of at least any of the above mentioned miRNAs is indicative of pancreatic cancer or intraductal papillary mucinous neoplasm of the pancreas (IPMN).

21 Claims, 14 Drawing Sheets

Specification includes a Sequence Listing.

(56) References Cited

OTHER PUBLICATIONS

Bartel, "MicroRNAs: Genomics, Biogenesis, Mechanism, and Function," *Cell* 116:281-297, 2004.
Costello et al., "New biomarkers and targets in pancreatic cancer and their application to treatment," *Nature Reviews Gastroenterology Hepatology* 9:435-444, 2012.
Di Leva et al., "microRNAs in cancer," *Annu Rev Pathol* 9:287-314, 2014. (33 pages).
Di Leva et al., "miRNA profiling of cancer," *Curr Opin Genet Dev.* 23(1):3-11, 2013. (14 pages).
Esquela-Kerscher et al., "Oncomirs—microRNAs with a role in cancer," *Nature Reviews Cancer* 6:259-269, 2006.
Esteller, "Non-coding RNAs in human disease," *Nature Reviews Genetics* 12:861-874, 2011.
Giovannetti et al., "High-Throughput MicroRNA (miRNAs) Arrays Unravel the Prognostic Role of MiR-211 in Pancreatic Cancer," *PLOS ONE* 7(11):1-12, 2012.
Giovannetti et al., "MicroRNA-21 in Pancreatic Cancer: Correlation with Clinical Outcome and Pharmacologic Aspects Underlying Its Role in the Modulation of Gemcitabine Activity," *Cancer Res* 70(11): 4528-4538, 2010. (12 pages).
Hezel et al., "Genetics and biology of pancreatic ductal adenocarcinoma," *Genes & Development* 20:1218-1249, 2006. (33 pages).
Jamieson et al., "MicroRNA Molecular Profiles Associated with Diagnosis, Clinicopathologic Criteria, and Overall Survival in Patients with Resectable Pancreatic Ductal Adenocarcinoma," *Clin Cancer Res* 18(2):534-545, 2012. (13 pages).
Papaconstantinou et al., "Expression of MicroRNAs in Patients with Pancreatic Cancer and Its Prognostic Significance," *Pancreas* 42(1):67-71, 2013.
Raimondi et al., "Epidemiology of pancreatic cancer: an overview," *Nature Reviews Gastroenterology & Hepatology* 6:699-708, 2009.
Seufferlein et al., "Pancreatic adenocarcinoma: ESMO-ESDO Clinical Practice Guidelines for diagnosis, treatment and follow-up," *Annals of Oncology* 23(7):vii33-vii40, 2012.
Stathis et al., "Advanced pancreatic carcinoma: current treatment and future challenges," *Nature Reviews Clinical Oncology* 7:163-172, 2010.
Vilmann et al., "Endoscopic ultrasound-guided fine needle aspiration biopsy: Equipment and technique," *Journal of Gastroenterology and Hepatology* 21:1646-1655, 2006.
Yu et al., "MicroRNA Alterations of Pancreatic Intraepithelial Neoplasms (PanINs)," *Clin Cancer Res.* 18(4):981-992, 2012. (21 pages).
Zhang et al., "Profiling of 95 MicroRNAs in Pancreatic Cancer Cell Lines and Surgical Specimens by Real Time PCR Analysis," *World J Surg.* 33(4):698-709, 2009. (18 pages).

\* cited by examiner

SEQUENCE LISTING

<160> NUMBER OF SEQ ID NOS: 1

<210> SEQ ID NO 1
<211> LENGTH: 22
<212> TYPE: RNA
<213> ORGANISM: Artificial Sequence
<220> FEATURE:

```
<223> OTHER INFORMATION: hsa-miR-33a*
<220> FEATURE:
<221> NAME/KEY: misc_feature
<222> LOCATION: (1)..(22)

<400> SEQUENCE: 1
caauguuucc acagugcauc ac                                              22
```

IN VITRO METHOD FOR IDENTIFYING PANCREATIC CANCER OR INTRADUCTAL PAPILLARY MUCINOUS NEOPLASM OF THE PANCREAS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 100222_401USPC_SEQUENCE_LISTING.txt. The text file is 514 bytes in size, was created on Oct. 23, 2018, and is being submitted electronically via EFS-Web.

FIELD OF THE INVENTION

The present invention can be included in the field of personalized medicine, wherein specific biomarkers are used for identifying a given disease or disorder. Specifically, some microRNAs (also named miRNAs or miR-) are used in the present invention for identifying human subjects at risk of developing pancreatic cancer or intraductal papillary mucinous neoplasm of the pancreas (IPMN), preferably pancreatic ductal adenocarcinoma (PDAC).

BACKGROUND OF THE INVENTION

Pancreatic ductal adenocarcinoma (PDAC) is the fourth leading cause of cancer death in occidental countries and has the worst prognosis of all major malignancies with just a 6% five-year survival rate. By the time of diagnosis, most patients present with locally advanced or metastatic disease that precludes curative resection and have a mean survival of less than 1 year {Stathis, #2281; Raimondi, 2009 #2150}. These dire statistics are due to high aggressiveness of the tumour, limited response to available treatments, resistance to chemotherapy and radiation in most cases and lack of methods for early detection {Hezel, 2006 #2114; Costello, #3039}.

Currently, the best available diagnostic tests include computed tomography (CT), magnetic resonance imaging (MM) combined with magnetic resonance cholangiopancreatography (MRCP) and endoscopic-ultrasound-guided fine needle aspiration biopsy (EUS-FNA) {Seufferlein, #3163}. Along with an increasing use of these imaging techniques, the diagnosis of intraductal papillary mucinous neoplasm (IPMN), the most common cystic precursor lesion of PDAC, has risen incessantly representing up to 25% of resected pancreatic neoplasms {Andrejevic-Blant, 2007 #3175}. However, they are not sensitive enough to assess for the malignity of an IPMN or to detect pancreatic cancer at an early stage of dysplasia {Vilmann, 2006 #3195}. Therefore, a deeper knowledge of molecular carcinogenesis of PDAC, novel early diagnostic biomarkers and effective therapeutic targets are urgently required to improve the outcome of this malignant disease.

MicroRNAs (miRNAs) are small endogenous non-coding RNAs of 19-25 nucleotides that negatively regulate gene expression at the posttranscriptional level by either repressing mRNA translation or targeting mRNAs for degradation {Bartel, 2004 #3178}. miRNAs are estimated to modulate the translation of more than 60% of protein-coding genes and are involved in regulating a wide range of biological processes such as cellular proliferation, differentiation, apoptosis and development {Esteller, #3179; Di Leva, #3158}. Their dysregulation play an essential role in the development and progression of cancer and they can act as tumour suppressors or oncogenes by targeting one or even hundreds of mRNAs {Esquela-Kerscher, 2006 #968}.

Aberrant expression of miRNAs has been widely reported in human cancers including PDAC and its precursor lesions {Zhang, 2009 #3189; Yu, #3183}. The differential expression of miRNAs between normal and malignant tissues can arise from chromosomal alterations of the miRNA genes, many of which are located at cancer-associated genomic regions, DNA point mutations, epigenetic mechanisms or alterations in the miRNA processing machinery {Di Leva, #3181}. Several studies of miRNA expression profiling have defined miRNA signatures for PDAC that are associated with diagnosis, staging, progression, prognosis and response to treatment {Jamieson, #3186; Giovannetti, #265; Papaconstantinou, #3193; Giovannetti, #3191}.

For this invention, we have analyzed for the first time the miRNome of PDAC and IPMN using the next generation sequencing technique. We have identified and discovered new candidate microRNAs as biomarkers for early detection of pancreatic cancer.

BRIEF DESCRIPTION OF THE INVENTION

The present invention offers a clear solution for accurately screening and diagnosing subjects at risk of having or developing pancreatic cancer, by means of a method, preferably minimally-invasive, able to detect not only patients at risk of suffering from pancreatic cancer but also patients which could suffer from intraductal papillary mucinous neoplasm (IPMN) and thus able to identify the subjects at risk at an early stage.

DETAILED DESCRIPTION OF THE INVENTION

Definitions

Figure 1:
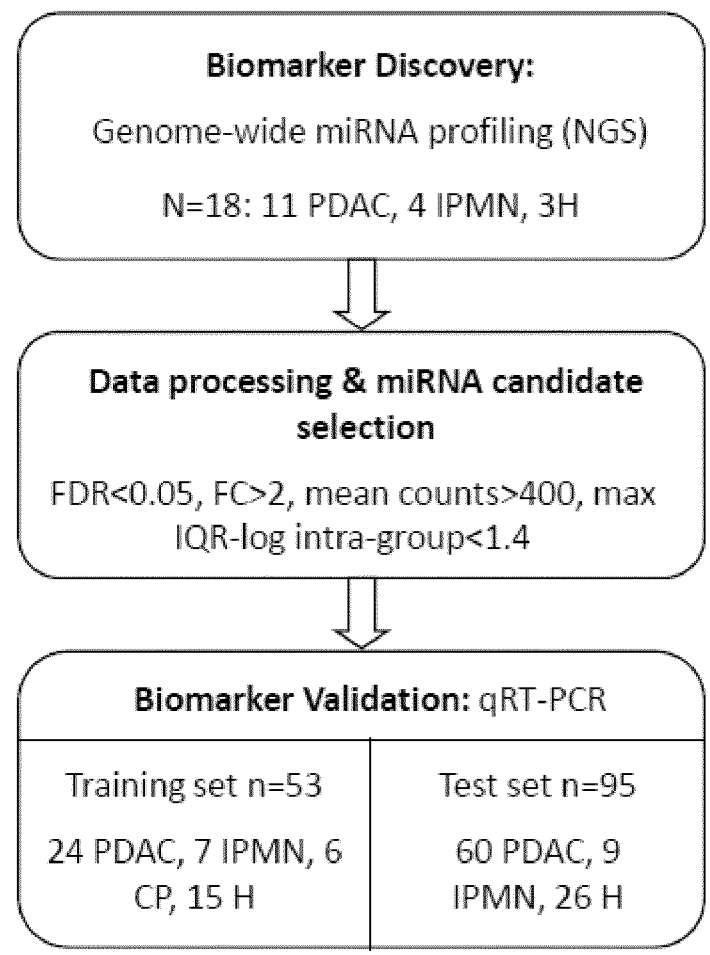
FIG. 1. A flowchart of the study design is shown. Next generation sequencing was performed on a set of pancreatic tissue samples for biomarker discovery. Candidate miRNAs were analyzed by qRT-PCR in 2 independent sets of samples. FDR: false discovery rate; FC: fold change; IQR: interquartile range.

For the purpose of the present invention, the following definitions are included below:

The term "screening" is understood as the examination or testing of a group of individuals pertaining to the general population, at risk of suffering from pancreatic cancer or intraductal papillary mucinous neoplasm of the pancreas (IPMN), preferably from pancreatic ductal adenocarcinoma (PDAC), with the objective of discriminating healthy individuals from those who are suffering from an undiagnosed pancreatic cancer or intraductal papillary mucinous neoplasm of the pancreas (IPMN), or who are at high risk of suffering from said indications.

The term "pancreatic cancer" is a synonym of the term "pancreatic neoplasia" and includes the well-accepted medical definition.

The expression "intraductal papillary mucinous neoplasm of the pancreas (IPMN)" refers to a type of tumor (neoplasm) that grows within the pancreatic ducts (intraductal) and is characterized by the production of thick fluid by the tumor cells (mucinous). Intraductal papillary mucinous neoplasms are important because if they are left untreated some of them progress to invasive cancer (transform from a benign tumor to a malignant tumor). Just as colon polyps can develop into colon cancer if left untreated, so too do some intraductal papillary mucinous neoplasms progress into an invasive pancreatic cancer. Intraductal papillary mucinous neoplasms can present an opportunity to treat a pancreatic tumor before it develops into an aggressive, hard-to-treat cancer.

The term "hsa-miR-33a*" is also herein referred to as hsa-miR-33a-3p MIMAT0004506 and consists of the following sequence: CAAUGUUUCCACAGUG-CAUCAC (SEQ ID NO: 1).

The expression "minimally-invasive biological sample" refers to any sample which is taken from the body of the patient without the need of using harmful instruments, other than fine needles used for taking the blood from the patient, and consequently without being harmfully for the patient. Specifically, minimally-invasive biological sample refers in the present invention to: blood, serum, or plasma samples.

The term "up-regulated" or "over-expressed" of any of the micro-RNAs or combinations thereof described in the present invention, refers to an increase in their expression level with respect to a given "threshold value" or "cutoff value" by at least 5%, by at least 10%, by at least 15%, by at least 20%, by at least 25%, by at least 30%, by at least 35%, by at least 40%, by at least 45%, by at least 50%, by at least 55%, by at least 60%>, by at least 65%>, by at least 70%, by at least 75%, by at least 80%, by at least 85%, by at least 90%, by at least 95%, by at least 100%, by at least 110%, by at least 120%, by at least 130%, by at least 140%, by at least 150%, or more.

The term "threshold value" or "cutoff value", when referring to the expression levels of the miRNAs described in the present invention, refers to a reference expression level indicative that a subject is likely to suffer from colorectal cancer or colorectal adenoma with a given sensitivity and specificity if the expression levels of the patient are above said threshold or cut-off or reference levels.

The term "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

It is also noted that the term "kit" as used herein is not limited to any specific device and includes any device suitable for working the invention such as but not limited to microarrays, bioarrays, biochips or biochip arrays.

A variety of statistical and mathematical methods for establishing the threshold or cutoff level of expression are known in the prior art. A threshold or cutoff expression level for a particular biomarker may be selected, for example, based on data from Receiver Operating Characteristic (ROC) plots, as described in the Examples and Figures of the present invention. One of skill in the art will appreciate that these threshold or cutoff expression levels can be varied, for example, by moving along the ROC plot for a particular biomarker or combinations thereof, to obtain different values for sensitivity or specificity thereby affecting overall assay performance. For example, if the objective is to have a robust diagnostic method from a clinical point of view, we should try to have a high sensitivity. However, if the goal is to have a cost-effective method we should try to get a high specificity. The best cutoff refers to the value obtained from the ROC plot for a particular biomarker that produces the best sensitivity and specificity. Sensitivity and specificity values are calculated over the range of thresholds (cutoffs). Thus, the threshold or cutoff values can be selected such that the sensitivity and/or specificity are at least about 70%, and can be, for example, at least 75%, at least 80%, at least 85%, at least 90%, at least 95%, at least 96%, at least 97%, at least 98%, at least 99% or at least 100% in at least 60% of the patient population assayed, or in at least 65%, 70%, 75% or 80% of the patient population assayed.

Consequently, each of the embodiments cited through-out the present invention is preferably carried out by determining the expression levels of at least the micro-RNAs cited in the present invention in a sample isolated from a subject to be diagnosed or screened, and comparing the expression levels of said micro-RNAs with predetermined threshold or cutoff values, wherein said predetermined threshold or cut-off values correspond to the expression level of said micro-RNAs which correlates with the highest specificity at a desired sensitivity in a ROC curve calculated based on the expression levels of the micro-RNAs determined in a patient population being at risk of developing pancreatic cancer or intraductal papillary mucinous neoplasm of the pancreas (IPMN), wherein the overexpression of at least one of said micro-RNAs with respect to said predetermined cutoff value is indicative that the subject suffers from pancreatic cancer or intraductal papillary mucinous neoplasm of the pancreas (IPMN) with said desired sensitivity.

DESCRIPTION

In this study, we have conducted genome-wide miRNA profiling by next-generation sequencing in a group of pancreatic samples including PDAC, IPMN and healthy pancreas. Our results show that tissue-based miRNA expression can discriminate between PDAC patients and control subjects, and also between patients with the precursor lesion IPMN and healthy individuals. To our knowledge, this is one of the first reports applying massive parallel sequencing for biomarker discovery in the context of pancreatic cancer. This high-throughput analysis has allowed the identification of a large number of putative miRNA biomarkers useful to detect patients harboring PDAC or IPMN. In addition, we have validated in 2 different groups of samples the expression pattern of 30 miRNAs, thus confirming their capacity of differentiating PDAC or IPMN from controls. In this sense, the list of the 30 highly discriminating microRNAs above mentioned, between PDAC or IPMN and healthy tissues is the following: miR-103a, miR-151a-5p, miR-155, miR-16, miR-181a, miR-181b, miR-192, miR-21, miR-221, miR-23a, miR-29a, miR-429, miR-93, miR-320a, let-7e, let-7f, miR-1257, miR-1304, miR-151b, miR-3120-3p, miR-3133, miR-33a*, miR-3714, miR-4468, miR-4639-5p, miR-4713-5p, miR-4714-5p, miR-4770, miR-548d-3p and miR-761. Some of these miRNAs represent novel biomarkers, not previously reported. Finally, we have defined the best miRNA-based predictors able to discriminate PDAC patients with high accuracy.

The first association of miRNAs and cancer came from a study of Calin et al. in which they characterized chromosome 13q14 in chronic lymphocytic leukemia (CLL) and showed that miR-15 and miR-16 are deleted or down-regulated in about 70% of CLL cases {Calin, 2002 #3180}. Since then, altered expression of miRNAs has been described in several human cancers such as those of breast, lung, esophagus, prostate and pancreas, among others {Piepoli, #3188}. Lu et al., carried out a systematic analysis of 217 miRNAs from 334 leukaemias and solid cancers, and found that miRNA-expression profiles classify human cancers according to the developmental lineage and differentiation state of the tumors {Lu, 2005 #1980}. In agreement with this, our genome-wide miRNome analysis has shown that PDAC, IPMN and healthy pancreatic tissue have a differential miRNA profile. In recent years, some studies focusing on large-scale profiles of miRNAs in pancreatic tissues have identified, mainly by microarrays, qRT-PCR cards or Genechips, a number of differentially expressed miRNAs. Despite differences in measurement platforms and lab protocols as well as sample sizes between previous reports and our study, we have been able to confirm published results from different studies. Among those 30 miRNAs validated by qRT-PCR, we have found concordant expression of previously reported miRNAs altered in PDAC tissue (i.e., upregulation of miR-103a, miR-151a-5p, miR-155, miR-16, miR-181a, miR-181b, miR-192, miR-21, miR-221, miR-23a, miR-29a, miR-429 and miR-93) {Jamieson, #3186; Piepoli, #3188; Bloomston, 2007 #3182; Szafranska, 2007 #3190; Lee, 2007 #3192; Bauer, #3207} but we have also identified several new miRNAs (17 miRNAs) that are significantly upregulated in PDAC (miR-320a, let-7e, let-7f, miR-1257, miR-1304, miR-151b, miR-3120-3p, miR-3133, miR-33a*, miR-3714, miR-4468, miR-4639-5p, miR-4713-5p, miR-4'714-5p, miR-4770, miR-548d-3p and miR-761).

In addition, table 1 below provides a comparison of the expression between PDAC or IPMN and healthy patients, of 17 miRNAs from the list of 30 miRNAs above mentioned, analyzed in a plasma set.

TABLE 1

Comparison of the expression between PDAC or IPMN and healthy patients.

| | Plasma set (qRT-PCR) | | | |
| --- | --- | --- | --- | --- |
| microRNA | FC PDAC vs H | FDR PDAC vs H | FC IPMN vs H | FDR IPMN vs H |
| hsa-let-7e | 1.49 | 1.7E−02 | 1.92 | 6.2E−04 |
| hsa-let-7f | 1.84 | 4.6E−03 | 2.25 | 2.5E−03 |
| hsa-miR-103a | 1.84 | 1.1E−03 | 3.43 | 5.6E−01 |
| hsa-miR-151a-5p | 1.79 | 7.6E−04 | 2.72 | 4.6E−04 |
| hsa-miR-151b | 1.95 | 5.1E−05 | 2.70 | 2.7E−04 |
| hsa-miR-155 | 1.26 | 2.0E−01 | 1.75 | 3.5E−04 |
| hsa-miR-16 | 2.12 | 3.1E−05 | 3.04 | 2.1E−04 |
| hsa-miR-181a | 1.87 | 2.5E−04 | 2.57 | 1.3E−03 |
| hsa-miR-181b | 4.57 | 4.2E−03 | 4.18 | 8.0E−04 |
| hsa-miR-192 | 3.57 | 6.8E−07 | 2.60 | 2.1E−03 |
| hsa-miR-21 | 3.19 | 1.4E−07 | 2.95 | 1.0E−01 |
| hsa-miR-221 | 2.35 | 5.9E−04 | 2.65 | 1.2E−03 |
| hsa-miR-23a | 1.71 | 1.8E−03 | 1.64 | 1.9E−02 |
| hsa-miR-320a | 2.65 | 3.8E−07 | 3.54 | 2.5E−02 |
| hsa-miR-33a* | 37.23 | 4.9E−08 | 25.69 | 2.3E−02 |
| hsa-miR-548d-3p | 3.29 | 1.0E−03 | 2.86 | 3.2E−04 |
| hsa-miR-93 | 2.21 | 4.8E−06 | 3.79 | 8.0E−04 |

In addition, table 2 below provides a ROC curve analysis of the above mentioned 17 miRNAs analysed in the plasma set.

TABLE 2

ROC curve analysis of the above mentioned 17 miRNAs analysed in the plasma set.

| | Plasma set (qRT-PCR) | | | | | |
| --- | --- | --- | --- | --- | --- | --- |
| microRNA | AUC (PDAC vs H) | 95% CI | p-value | AUC (IPMN vs H) | 95% CI | p-value |
| hsa-let-7e | 0.716 | 0.757-0.675 | 1.8E−05 | 0.689 | 0.762-0.617 | 1.5E−02 |
| hsa-let-7f | 0.722 | 0.762-0.681 | 1.1E−05 | 0.695 | 0.767-0.623 | 1.3E−02 |
| hsa-miR-103a | 0.743 | 0.782-0.704 | 1.4E−06 | 0.823 | 0.883-0.762 | 3.7E−05 |
| hsa-miR-151a-5p | 0.745 | 0.784-0.706 | 1.1E−06 | 0.779 | 0.844-0.714 | 3.6E−04 |
| hsa-miR-151b | 0.778 | 0.814-0.741 | 3.6E−08 | 0.783 | 0.848-0.718 | 3.0E−04 |
| hsa-miR-155 | 0.669 | 0.713-0.626 | 7.7E−04 | 0.692 | 0.764-0.619 | 1.4E−02 |
| hsa-miR-16 | 0.770 | 0.807-0.733 | 8.1E−08 | 0.817 | 0.878-0.756 | 4.9E−05 |
| hsa-miR-181a | 0.756 | 0.794-0.718 | 3.6E−07 | 0.755 | 0.822-0.687 | 1.1E−03 |
| hsa-miR-181b | 0.725 | 0.766-0.685 | 1.1E−05 | 0.693 | 0.766-0.621 | 1.4E−02 |
| hsa-miR-192 | 0.825 | 0.857-0.793 | 1.1E−10 | 0.761 | 0.828-0.694 | 8.4E−04 |
| hsa-miR-21 | 0.862 | 0.890-0.834 | 6.6E−13 | 0.833 | 0.892-0.774 | 2.1E−05 |
| hsa-miR-221 | 0.741 | 0.781-0.702 | 1.9E−06 | 0.704 | 0.776-0.633 | 9.1E−03 |
| hsa-miR-23a | 0.742 | 0.781-0.703 | 1.5E−06 | 0.674 | 0.747-0.600 | 2.6E−02 |

TABLE 2-continued

ROC curve analysis of the above mentioned 17 miRNAs analysed in the plasma set.

| microRNA | Plasma set (qRT-PCR) | | | | | |
|---|---|---|---|---|---|---|
| | AUC (PDAC vs H) | 95% CI | p-value | AUC (IPMN vs H) | 95% CI | p-value |
| hsa-miR-320a | 0.849 | 0.879-0.819 | 4.3E−12 | 0.894 | 0.943-0.845 | 4.6E−07 |
| hsa-miR-33a* | 0.857 | 0.886-0.828 | 1.9E−12 | 0.820 | 0.881-0.759 | 4.5E−05 |
| hsa-miR-548d-3p | 0.762 | 0.802-0.722 | 7.4E−07 | 0.723 | 0.804-0.643 | 1.1E−02 |
| hsa-miR-93 | 0.790 | 0.826-0.755 | 8.3E−09 | 0.844 | 0.901-0.786 | 1.1E−05 |

Moreover, we herein provide a ROC curve analysis of the best miRNAs combinations from the above mentioned plasma set (see table 3 below).

TABLE 3

ROC curve analysis of the best miRNAs combinations from the plasma set of table 1.

| microRNA | AUC (PDAC vs H) | 95% CI | AUC (IPMN vs H) | 95% CI |
|---|---|---|---|---|
| hsa.miR.320a + hsa.miR.33a* | 0.902 | 0.959-0.846 | 0.904 | 0.973-0.835 |
| hsa.miR.16 + hsa.miR.320a + hsa.miR.33a* | 0.922 | 0.969-0.875 | 0.917 | 0.979-0.855 |
| hsa.miR.320a + hsa.miR.181a + hsa.miR.33a* | 0.919 | 0.969-0.868 | 0.937 | 0.990-0.884 |
| hsa.miR.320a + hsa.miR.33a* + hsa.miR.155 | 0.917 | 0.969-0.865 | 0.919 | 0.981-0.857 |
| hsa.miR.320a + hsa.miR.151b + hsa.miR.33a* | 0.916 | 0.969-0.862 | 0.923 | 0.984-0.862 |
| hsa.miR.320a + hsa.let.7e + hsa.miR.33a* | 0.918 | 0.967-0.870 | 0.927 | 0.985-0.870 |
| hsa.miR.320a + hsa.miR.23a + hsa.miR.33a* | 0.912 | 0.967-0.857 | 0.923 | 0.983-0.863 |
| hsa.miR.320a + hsa.miR.151a.5p + hsa.miR.33a* | 0.913 | 0.965-0.861 | 0.909 | 0.976-0.843 |
| hsa.let.7e + hsa.miR.21 + hsa.miR.33a* | 0.923 | 0.966-0.881 | 0.904 | 0.972-0.836 |
| hsa.miR.23a + hsa.miR.21 + hsa.miR.33a* | 0.915 | 0.963-0.867 | 0.906 | 0.973-0.839 |
| hsa.miR.93 + hsa.miR.320a + hsa.miR.33a* | 0.911 | 0.963-0.859 | 0.899 | 0.970-0.828 |

Furthermore, due to the increasing incidence and the high risk of malignancy that IPMN lesions present, we aimed to investigate the miRNome of IPMNs along with PDAC in order to identify candidate miRNAs for detection of both pancreatic neoplasias. So far, few studies have analyzed miRNA expression in IPMN. Habbe et al. demonstrated significant overexpression of 10 miRNAs out of 12 analyzed for being upregulated in pancreatic cancer {Habbe, 2009 #2164}. Matthaei H el al. and Lubezky S et al. showed that certain miRNAs have a different expression level in low-grade versus high-grade IPMNs, which may be used as markers for invasiveness {Matthaei, #3184; Lubezky, #3185}.

Our NGS results have demonstrated that PDAC and IPMN lesions share 325 significantly deregulated miRNAs. This indicates that aberrant miRNA expression occurs early in the pancreatic cancer development. From the 30 miRNAs validated as significantly upregulated in IPMNs, 6 had already been described (i.e., miR-155, miR-16, miR-181a, miR-21, miR-221, and miR-93) {Habbe, 2009 #2164; Matthaei, #3184; Lubezky, #3185; Caponi, #3187}. However, the other 24 miRNAs found deregulated in IPMN had not been previously reported.

To ensure reliable results, we have corroborated the same expression pattern of all 30 miRNAs previously mentioned in 3 independent sample sets (NGS, training and test set), and consequently we have observed that the differential miRNA profile in frozen tissue samples correlates well with the one in EUS-FNA samples. Szafranska et al. reported that miRNA analysis from fresh pancreatic FNA biopsies differentiated malignant from benign tissues {Szafranska, 2008 #271}. Ali et al. validated the expression of 7 miRNAs in formalin-fixed paraffinembedded (FFPE) cell blocks from diagnostic FNAs of PDAC {Ali, #3112}.

Accordingly, our study affirms the feasibility of detecting miRNAs in FNA samples by undergoing validation of a larger number of miRNAs in a bigger cohort. It is remarkable to point out the high discriminative accuracy for PDAC of miR-93, miR16, miR-548d-3p and miR-320a with AUC over 0.95 in the test set. Their performance in the training set, even though presenting AUC over 0.8, is not as accurately as in the test set owing to differences in the clinical characteristics of the patients.

In summary, this study identifies novel miRNAs commonly deregulated in PDAC and IPMN biological samples such as tumor sample or of a minimally-invasive biological sample such as a plasma sample, blood sample, Cerebrospinal fluid (CSF) sample or a serum sample, with potential utility as diagnostic biomarkers. Moreover, new therapeutic targets could emerge from these results.

Thus, a first aspect of the invention refers to an in vitro method for screening for subjects at risk of developing pancreatic cancer or intraductal papillary mucinous neoplasm of the pancreas (IPMN) comprising: (a) measuring the expression pattern or level of at least hsa-miR-33a*, or of at least hsa-miR-320a, or of at least hsa-let-7e, or of at least hsa-let-7f, or of at least hsa-miR-1257, or of at least hsa-miR-1304, or of at least hsa-miR-151b, or of at least hsa-miR-3120-3p, or of at least hsa-miR-3133, or of at least hsa-miR-3714, or of at least hsa-miR-4468, or of at least hsa-miR-4639-5p, or of at least hsa-miR-4713-5p, or of at least hsa-miR-4714-5p, or of at least hsa-miR-4770, or of at least hsa-miR-548d-3p, or of at least hsa-miR-761, obtained from an isolated biological sample of the subjects to be screened; and (b) comparing said expression pattern or level of at least hsa-miR-33a*, or of at least hsa-miR-320a, or of at least hsa-let-7e, or of at least hsa-let-7f, or of at least hsa-miR-1257, or of at least hsa-miR-1304, or of at least hsa-miR-151b, or of at least hsa-miR-3120-3p, or of at least hsa-miR-3133, or of at least hsa-miR-3714, or of at least hsa-miR-4468, or of at least hsa-miR-4639-5p, or of at least hsa-miR-4713-5p, or of at least hsa-miR-4714-5p, or of at least hsa-miR-4770, or of at least hsa-miR-548d-3p, or of at least hsa-miR-761, of the subjects to be screened with an already established expression pattern or level, wherein overexpression of at least any of the above mentioned miRNAs is indicative of pancreatic cancer or intraductal papillary mucinous neoplasm of the pancreas (IPMN).

In a preferred embodiment of the first aspect of the invention, the in vitro method for screening subjects, comprises: (a) measuring the expression pattern or level of at least hsa-miR-33a* and at least one or more of the following group of miRNAs: hsa-let-7c, hsa-let-7e, hsa-let-7f, hsa-miR-103a, hsa-miR-1257, hsa-miR-1304, hsa-miR-151a-5p, hsa-miR-151b, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-3120-3p, hsa-miR-3133, hsa-miR-3145-3p, hsa-miR-320a, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least miR-33a* and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-320a and at least one or more of the following group of miRNAs: hsa-let-7c, hsa-let-7e, hsa-let-7f, hsa-miR-103a, hsa-miR-1257, hsa-miR-1304, hsa-miR-151a-5p, hsa-miR-151b, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-3120-3p, hsa-miR-3133, hsa-miR-3145-3p, hsa-miR-33a*, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-320a and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-let-7e and at least one or more of the following group of miRNAs: hsa-let-7c, hsa-miR-33a*, hsa-let-7f, hsa-miR-103a, hsa-miR-1257, hsa-miR-1304, hsa-miR-151a-5p, hsa-miR-151b, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-3120-3p, hsa-miR-3133, hsa-miR-3145-3p, hsa-miR-320a, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-let-7e and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-let-7f and at least one or more of the following group of miRNAs: hsa-let-7c, hsa-let-7e, hsa-miR-33a*, hsa-miR-103a, hsa-miR-1257, hsa-miR-1304, hsa-miR-151a-5p, hsa-miR-151b, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-3120-3p, hsa-miR-3133, hsa-miR-3145-3p, hsa-miR-320a, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-let-7f and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-1257 and at least one or more of the following group of miRNAs: hsa-let-7c, hsa-let-7e, hsa-let-7f, hsa-miR-103a, hsa-miR-33a*, hsa-miR-1304, hsa-miR-151a-5p, hsa-miR-151b, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-3120-3p, hsa-miR-3133, hsa-miR-3145-3p, hsa-miR-320a, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-1257 and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-1304 and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-151b, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-3120-3p, hsa-miR-3133, hsa-miR-3145-3p, hsa-miR-320a, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-1304 and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-151b and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-3120-3p, hsa-miR-3133, hsa-miR-3145-3p, hsa-miR-320a, hsamiR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-151b and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-3120-3p and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3133, hsa-miR-3145-3p, hsa-miR-320a, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-3120-3p and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-3133 and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-3133 and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-3714 and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-3714 and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-4468 and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-4468 and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-4639-5p and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-4639-5p and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-4'713-5p and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-4713-5p and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-4714-5p and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR- 320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4770, hsa-miR-4801, hsa-miR-548d-3p, hsa-miR-616*, hsa-miR-761 and hsa-miR-93, wherein overexpression of at least hsa-miR-4714-5p and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-4770 and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-548d-3p, hsa-miR-616*, hsa-miR-761 and hsa-miR-93, wherein overexpression of at least hsa-miR-4770 and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-548d-3p and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-4770, hsa-miR-616*, hsa-miR-761 and hsa-miR-93, wherein overexpression of at least hsa-miR-548d-3p and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-761 and at least one or more of the following group of miRNAs: hsa-let-7c, hsa-let-7e, hsa-let-7f, hsa-miR-103a, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-4770, hsa-miR-616*, hsa-miR-548d-3p and hsa-miR-93, wherein overexpression of at least hsa-miR-761 and at least one of the biomarkers identified above is indicative of pancreatic cancer or intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-33a* and hsa-miR-320a, or of at least hsa-miR-33a* and hsa-miR-16 and hsa-miR-320a, or of at least hsa-miR-33a* and hsa-miR-320a and hsa-miR-181, or of at least hsa-miR-33a* and hsa-miR-320a and hsa-miR-155, or of at least hsa-miR-33a* and hsa-miR-320a and hsa-miR-151b, or of at least hsa-miR-33a* and hsa-miR-320a and hsa-let7e, or of at least hsa-miR-33a* and hsa-miR-320a and hsa-miR-23a, or of at least hsa-miR-33a* and hsa-miR-320a and hsa-miR-151a, or of at least hsa-miR-33a* and hsa-miR-21 and hsa-let7e, or of at least hsa-miR-33a* and hsa-miR-23a and hsa-miR-21, or of at least hsa-miR-33a* and hsa-miR-93 and hsa-miR-320a, obtained from an isolated biological sample of the subjects to be screened; and (b) comparing said expression pattern or level of at least hsa-miR-33a* and hsa-miR-320a, or of at least hsa-miR-33a* and hsa-miR-16 and hsa-miR-320a, or of at least hsa-miR-33a* and hsa-miR-320a and hsa-miR-181, or of at least hsa-miR-33a* and hsa-miR-320a and hsa-miR-155, or of at least hsa-miR-33a* and hsa-miR-320a and hsa-miR-151b, or of at least hsa-miR-33a* and hsa-miR-320a and hsa-let7e, or of at least hsa-miR-33a* and hsa-miR-320a and hsa-miR-23a, or of at least hsa-miR-33a* and hsa-miR-320a and hsa-miR-151a, or of at least hsa-miR-33a* and hsa-miR-21 and hsa-let7e, or of at least hsa-miR-33a* and hsa-miR-23a and hsa-miR-21, or of at least hsa-miR-33a* and hsa-miR-93 and hsa-miR-320a, of the subjects to be screened with an already established expression pattern or level, wherein overexpression of at least hsa-miR-33a* and hsa-miR-320a, or of at least hsa-miR-33a* and hsa-miR-16 and hsa-miR-320a, or of at least hsa-miR-33a* and hsa-miR-320a and hsa-miR-181, or of at least hsa-miR-33a* and hsa-miR-320a and hsa-miR-155, or of at least hsa-miR-33a* and hsa-miR-320a and hsa-miR-151b, or of at least hsa-miR-33a* and hsa-miR-320a and hsa-let7e, or of at least hsa-miR-33a* and hsa-miR-320a and hsa-miR-23a, or of at least hsa-miR-33a* and hsa-miR-320a and hsa-miR-151a, or of at least hsa-miR-33a* and hsa-miR-21 and hsa-let7e, or of at least hsa-miR-33a* and hsa-miR-23a and hsa-miR-21, or of at least hsa-miR-33a* and hsa-miR-93 and hsa-miR-320a, is indicative of pancreatic cancer or intraductal papillary mucinous neoplasm of the pancreas (IPMN).

Another preferred embodiment of the invention refers to an in vitro method for screening for subjects at risk of developing intraductal papillary mucinous neoplasm of the pancreas (IPMN) comprising: (a) measuring the expression pattern or level of at least hsa-miR-103a, or of at least hsa-miR-151a-5p, or of at least hsa-miR-181b, or of at least hsa-miR-192, or of at least hsa-miR-23a, or of at least hsa-miR-29a, or of at least hsa-miR-429, obtained from an isolated biological sample of the subjects to be screened; and (b) comparing said expression pattern or level of at least hsa-miR-103a, or of at least hsa-miR-151a-5p, or of at least hsa-miR-181b, or of at least hsa-miR-192, or of at least hsa-miR-23a, or of at least hsa-miR-29a, or of at least hsa-miR-429, of the subjects to be screened with an already established expression pattern or level, wherein overexpression of at least any of the above mentioned miRNAs is indicative of intraductal papillary mucinous neoplasm of the pancreas (IPMN).

In yet another preferred embodiment of the first aspect of the invention, the in vitro method for screening subjects, comprises: (a) measuring the expression pattern or level of at least hsa-miR-103a and at least one or more of the following group of miRNAs: hsa-let-7c, hsa-let-7e, hsa-let- 7f, hsa-miR-761, hsa-miR-33a*, hsa-miR-1257, hsa-miR-151a-5p, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-4770, hsa-miR-616*, hsa-miR-548d-3p and hsa-miR-93, wherein overexpression of at least hsa-miR-103a and at least one of the biomarkers identified above is indicative of intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-151a-5p and at least one or more of the following group of miRNAs: hsa-let-7c, hsa-let-7e, hsa-let-7f, hsa-miR-761, hsa-miR-33a*, hsa-miR-1257, hsa-miR-103a, hsa-miR-1304, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-4770, hsa-miR-616*, hsa-miR-548d-3p and hsa-miR-93, wherein overexpression of at least hsa-miR-151a-5p and at least one of the biomarkers identified above is indicative of intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-181b and at least one or more of the following group of miRNAs: hsa-let-7c, hsa-let-7e, hsa-let-7f, hsa-miR-761, hsa-miR-33a*, hsa-miR-1257, hsa-miR-103a, hsa-miR-1304, hsa-miR-155, hsa-miR-16, hsa-miR-181, hsa-miR-181a, hsa-miR-151a-5p, hsa-miR-192, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-4770, hsa-miR-616*, hsa-miR-548d-3p and hsa-miR-93, wherein overexpression of at least hsa-miR-181b and at least one of the biomarkers identified above is indicative of intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-192 and at least one or more of the following group of miRNAs: hsa-let-7c, hsa-let-7e, hsa-let-7f, hsa-miR-761, hsa-miR-33a*, hsa-miR-1257, hsa-miR-103a, hsa-miR-1304, hsa-miR-155, hsa-miR-16, hsa-miR-181, hsa-miR-181a, hsa-miR-151a-5p, hsa-miR-181b, hsa-miR-21, hsa-miR-221, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-4770, hsa-miR-616*, hsa-miR-548d-3p and hsa-miR-93, wherein overexpression of at least hsa-miR-192 and at least one of the biomarkers identified above is indicative of intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-23a and at least one or more of the following group of miRNAs: hsa-let-7c, hsa-let-7e, hsa-let-7f, hsa-miR-761, hsa-miR-33a*, hsa-miR-1257, hsa-miR-103a, hsa-miR-1304, hsa-miR-155, hsa-miR-16, hsa-miR-181, hsa-miR-181a, hsa-miR-151a-5p, hsa-miR-181b, hsa-miR-21, hsa-miR-221, hsa-miR-192, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-4770, hsa-miR-616*, hsa-miR-548d-3p and hsa-miR-93, wherein overexpression of at least hsa-miR-23a and at least one of the biomarkers identified above is indicative of intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-29a and at least one or more of the following group of miRNAs: hsa-let-7c, hsa-let-7e, hsa-let-7f, hsa-miR-761, hsa-miR-33a*, hsa-miR-1257, hsa-miR-103a, hsa-miR-1304, hsa-miR-155, hsa-miR-16, hsa-miR-181, hsa-miR-181a, hsa-miR-151a-5p, hsa-miR-181b, hsa-miR-21, hsa-miR-221, hsa-miR-192, hsa-miR-23a, hsa-miR-151b, hsa-miR-3120-3p, hsa-miR-3145-3p, hsa-miR-320a, hsa-miR-3692, hsa-miR-3133, hsa-miR-4256, hsa-miR-429, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-4770, hsa-miR-616*, hsa-miR-548d-3p and hsa-miR-93, wherein overexpression of at least hsa-miR-29a and at least one of the biomarkers identified above is indicative of intraductal papillary mucinous neoplasm of the pancreas (IPMN).

In another preferred embodiment of the first aspect of the invention, the in vitro method for screening subjects, comprises: (a) measuring the expression pattern or level of at least hsa-miR-429 and at least one or more of the following group of miRNAs: hsa-let-7c, hsa-let-7e, hsa-let-7f, hsa-miR-761, hsa-miR-33a*, hsa-miR-1257, hsa-miR-103a, hsa-miR-1304, hsa-miR-155, hsa-miR-16, hsa-miR-181, hsa-miR-181a, hsa-miR-151a-5p, hsa-miR-181b, hsa-miR-21, hsa-miR-221, hsa-miR-192, hsa-miR-23a, hsa-miR-29a, hsa-miR-151b, hsa-miR-3120-3p, hsa-miR-3145-3p, hsa-miR-320a, hsa-miR-3692, hsa-miR-3133, hsa-miR-4256, hsa-miR-29a, hsa-miR-4313, hsa-miR-3714, hsa-miR-4468, hsa-miR-4642, hsa-miR-4666-3p, hsa-miR-4639-5p, hsa-miR-4713-5p, hsa-miR-4723-5p, hsa-miR-4714-5p, hsa-miR-4801, hsa-miR-4770, hsa-miR-616*, hsa-miR-548d-3p and hsa-miR-93, wherein overexpression of at least hsa-miR-429 and at least one of the biomarkers identified above is indicative of intraductal papillary mucinous neoplasm of the pancreas (IPMN).

A second aspect of the invention, refers to the in vitro method for the diagnosis of a subject suspected of suffering from pancreatic cancer or intra-ductal papillary mucinous neoplasm of the pancreas (IPMN) comprising the steps a) and b) of any of the methods of the first aspect of the invention or of any of its preferred embodiments, and optionally (c) confirming the presence of pancreatic cancer or intraductal papillary mucinous neoplasm of the pancreas (IPMN) by means of a clinical examination.

A third aspect of the invention refers to a method for obtaining useful data for the in vitro diagnosis of pancreatic cancer or intraductal papillary mucinous neoplasm of the pancreas (IPMN) comprising the steps a) and b) of any of the methods of the first aspect of the invention or of any of its preferred embodiments.

A fourth aspect of the invention, refers to an in vitro method for classifying subjects as healthy subjects or as subjects suffering from pancreatic cancer or intraductal papillary mucinous neoplasm of the pancreas (IPMN) comprising the steps a) and b) of any of the methods of the first aspect of the invention or of any of its preferred embodiments.

A fifth aspect of the invention, refers to an in vitro method for monitoring the response to a therapy or for monitoring the progression of pancreatic cancer or intraductal papillary mucinous neoplasm of the pancreas (IPMN) in a subject suffering from pancreatic cancer or intraductal papillary mucinous neoplasm of the pancreas (IPMN) comprising the steps a) and b) of any of the methods of the first aspect of the invention or of any of its preferred embodiments.

A sixth aspect of the invention refers to a method for treating subjects suffering from pancreatic cancer or intraductal papillary mucinous neoplasm of the pancreas (IPMN) comprising the steps a) and b) of any of the methods of the first aspect of the invention or of any of its preferred embodiments, and (c) treating the patient diagnosed with pancreatic cancer or intraductal papillary mucinous neoplasm of the pancreas (IPMN). Preferably, the patient is treated by surgery, chemotherapy or radiation.

In a preferred embodiment of the method, according to any of any of the methods of the first to sixth aspects of the invention or of any of its preferred embodiments, the pancreatic cancer is pancreatic ductal adenocarcinoma (PDAC).

In another preferred embodiment of the method, according to any of any of the methods of the first to fifth aspects of the invention or of any of its preferred embodiments, the biological sample is selected from the group consisting of a tumor sample or of a minimally-invasive biological sample of the subjects to be screened such as a plasma sample, blood sample, Cerebrospinal fluid (CSF) sample or a serum sample.

In yet another preferred embodiment of the method, according to any of any of the methods of the first to sixth aspects of the invention or of any of its preferred embodiments, the subject is a human subject.

A seventh aspect of the invention, refers to the use of a kit comprising biomarker detecting reagents for determining a differential expression level of any of the biomarkers or any of the combination of biomarkers mentioned in the methods of the first aspect of the invention or in any of its preferred embodiments, wherein overexpression of any of these biomarkers is indicative of pancreatic cancer or intraductal papillary mucinous neoplasm of the pancreas (IPMN), for diagnosing in vitro the risk for pancreatic cancer or intraductal papillary mucinous neoplasm of the pancreas (IPMN), preferably of pancreatic ductal adenocarcinoma.

A preferred embodiment of the seventh aspect of the invention, refers to the use of the kit, wherein said kit comprises reagents for determining a differential expression level of at least hsa-miR-33a* and at least hsa-miR-320a and/or at least hsa-let-7e and optionally at least one or more of the following group of miRNAs: hsa-let-7c, hsa-let-7f, hsa-miR-103a, hsa-miR-1257, hsa-miR-1304, hsa-miR-151a-5p, hsa-miR-151b, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-3120-3p, hsa-miR-3133, hsa-miR-3145-3p, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761 and hsa-miR-93, for diagnosing in vitro the risk for pancreatic cancer or intraductal papillary mucinous neoplasm of the pancreas (IPMN).

Another preferred embodiment of the seventh aspect of the invention, refers to the use of the kit, comprising reagents for determining a differential expression level of at least hsa-miR-33a* and hsa-miR-320a, or of at least hsa-miR-33a* and hsa-miR-16 and hsa-miR-320a, or of at least hsa-miR-33a* and hsa-miR-320a and hsa-miR-181, or of at least hsa-miR-33a* and hsa-miR-320a and hsa-miR-155, or of at least hsa-miR-33a* and hsa-miR-320a and hsa-miR-151b, or of at least hsa-miR-33a* and hsa-miR-320a and hsa-let7e, or of at least hsa-miR-33a* and hsa-miR-320a and hsa-miR-23a, or of at least hsa-miR-33a* and hsa-miR-320a and hsa-miR-151a, or of at least hsa-miR-33a* and hsa-miR-21 and hsa-let7e, or of at least hsa-miR-33a* and hsa-miR-23a and hsa-miR-21, or of at least hsa-miR-33a* and hsa-miR-93 and hsa-miR-320a, obtained from an isolated biological sample of the subjects to be screened, for diagnosing in vitro the risk for pancreatic cancer or intraductal papillary mucinous neoplasm of the pancreas (IPMN).

An eight aspect of the invention refers to a kit comprising biomarker detecting reagents for determining a differential expression level of one or more miRNAs selected from the group consisting of: hsa-miR-33a* and hsa-miR-320a, or of at least hsa-miR-33a* and hsa-miR-16 and hsa-miR-320a, or of at least hsa-miR-33a* and hsa-miR-320a and hsa-miR-181, or of at least hsa-miR-33a* and hsa-miR-320a and hsa-miR-155, or of at least hsa-miR-33a* and hsa-miR-320a and hsa-miR-151b, or of at least hsa-miR-33a* and hsa-miR-320a and hsa-let7e, or of at least hsa-miR-33a* and hsa-miR-320a and hsa-miR-23a, or of at least hsa-miR-33a* and hsa-miR-320a and hsa-miR-151a, or of at least hsa-miR-33a* and hsa-miR-21 and hsa-let7e, or of at least hsa-miR-33a* and hsa-miR-23a and hsa-miR-21, or of at least hsa-miR-33a* and hsa-miR-93 and hsa-miR-320a.

In a preferred embodiment of the eighth aspect of the invention or to the use of the kit according to the seventh aspect of the invention or to any of its preferred embodiments, such reagents are selected from the group consisting of all or of at least one of the following: i) specific primers to the miRNA or combinations of miRNAs as defined in any of said aspects or preferred embodiments capable of producing primer-ligated miRNA sequences; ii) reverse transcribing means to produce cDNAs from the primer-ligated miRNA sequences of i); iii) means such as primers capable of amplifying the cDNAs derived from the primer-ligated miRNA sequences as defined in i); iv) means to transcribe the amplified cDNAs to produce sense target RNAs; and v) a population of miRNA antisense probes capable of detecting the sense target RNAs of iv).

On the other hand, it is worth mentioning that the present invention is preferably carried out in plasma or serum samples obtained from the patients. On the other hand, it is important to emphasize that obtaining serum or plasma preparations from blood comprises several steps carried out by technicians: in the case of serum, allowing the blood to clot by leaving it undisturbed at room temperature, removing the clot by centrifuging and isolating the supernatant which is designed as serum. In the case of plasma, centrifugation is also needed. Moreover, after the centrifugation process, it is important to immediately transfer the liquid component (serum or plasma) into a clean tube. The samples are maintained at 2-8° C. while handling. If the serum or plasma is not analyzed immediately, it should be apportioned into aliquots, stored, and transported at −80° C. or lower. It is important to avoid freeze-thaw cycles because this is detrimental to many serum components. Samples which are hemolyzed, icteric or lipemic can invalidate certain tests.

On the other hand, it is important to note that nowadays the gold standard method for the diagnosis of pancreatic cancer is based on image techniques (CT or MRI) already described throughout the present application combined with MRCP and EUS-FNA. Nevertheless, said standard method is not sensitive enough to assess for the malignity of an IPMN or to detect pancreatic cancer at an early stage of dysplasia, and tools aimed at confirming the diagnosis obtained by using said techniques are needed. Thus, a preferred embodiment of the present invention is directed to a method for detecting and/or confirming IPMN or to detect and/or confirm pancreatic cancer in a subject, the method comprising the steps of: a) performing an image technique and/or a biopsy on the subject and b) measuring an expression level of the above cited miRNAs of the invention in biological sample obtained from the subject that is greater than the expression level of said miRNAs in a control sample obtained from a subject not having IPMN or pancreatic cancer. For example, sometimes the image obtained during the step a) is not clear enough to differentiate pancreatitis from pancreatic cancer and, consequently, the step b) is needed for confirming that the patient is suffering from pancreatic cancer (and for discarding pancreatitis).

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of groups, those skilled in the art will recognize that the invention is also thereby described in terms of any individual member or subgroup of members of the group.

EXAMPLES

Materials and Methods
Patients and Sample Collection

A total of 165 patients from Hospital Clinic of Barcelona were prospectively included in this study from February 2008 to January 2013. We obtained pancreatic samples from all subjects. None of these had received chemo or radiotherapy before sample collection. An initial set of 18 surgical macrodissected pancreatic tissue samples (11 PDAC; 4 IPMN; 3 healthy controls (H)) was used for genome-wide miRNA profiling. Normal pancreatic samples (H) correspond to either the adjacent non-tumor tissues of some PDAC and IPMN lesions or to the healthy tissue of patients who underwent surgery for other reasons (i.e., ampulloma or cystadenoma).

Validation of candidate miRNAs was done by quantitative reverse transcriptase PCR (qRT-PCR) in 2 other independent cohorts: a training set of 52 tissue samples (24 PDAC; 7 IPMN; 6 CP (chronic pancreatitis), 15H) and a test set of 95 endoscopic ultrasonography-guided fine needle aspiration (EUS-FNA) samples (60 PDAC; 9 IPMN; 26 H). FNA was performed using a standard 22G needle. Pancreatic tissues were kept on dry ice at all times during handling and all samples were flash frozen in liquid nitrogen and stored at −80° C. until RNA isolation. The clinicopathologic features of participants included in the study are detailed in table 4 below.

TABLE 4

| | Clinicopathologic characteristics of patients | | | | |
|---|---|---|---|---|---|
| | NGS set | | | Training set | |
| Characteristic | Healthy (n = 3) | IPMN (n = 4) | PDAC (n = 11) | Healthy (n = 15) | CP (n = 6) |
| Demographic | | | | | |
| Age, mean (SD) | 70.3 (5.0) | 61.5 (13.9) | 69.3 (10.6) | 66.5 (13.2) | 43.2 (6.5) |
| Sex, n (%) | | | | | |
| Males | 2 (66.7) | 1 (25) | 8 (72.7) | 5 (33.3) | 4 (66.7) |
| Females | 1 (33.3) | 3 (75) | 3 (27.3) | 10 (66.7) | 2 (33.3) |

TABLE 4-continued

Clinicopathologic characteristics of patients

| Pathologic Stage, n | | |
|---|---|---|
| I | 4 | 7 |
| II | | 3 |
| III | | 1 |
| IV | | |
| Unknown | | |
| Resectability, n | | |
| Yes | 4 | 10 |
| No | | 1 |
| Unknown | | |

| | Training set | | Test set | | |
|---|---|---|---|---|---|
| Characteristic | IPMN (n = 7) | PDAC (n = 24) | Healthy (n = 26) | IPMN (n = 9) | PDAC (n = 60) |
| Demographic | | | | | |
| Age, mean (SD) | 60.7 (11.9) | 63.3 (11.8) | 59.6 (17.1) | 66.6 (8.1) | 65.4 (11.5) |
| Sex, n (%) | | | | | |
| Males | 2 (28.6) | 17 (70.8) | 14 (53.8) | 4 (44.4) | 37 (61.7) |
| Females | 5 (71.4) | 7 (29.2) | 12 (46.2) | 5 (55.6) | 23 (38.3) |
| Pathologic Stage, n | | | | | |
| I | 7 | 10 | | 9 | 8 |
| II | | 3 | | | 8 |
| III | | 5 | | | 17 |
| IV | | 6 | | | 17 |
| Unknown | | | | | 10 |
| Resectability, n | | | | | |
| Yes | 7 | 15 | | 9 | 19 |
| No | | 9 | | | 33 |
| Unknown | | | | | 8 |

This study was approved by the Institutional Ethics Committee of Hospital Clinic of Barcelona and written informed consent was obtained from all patients in accordance with the Declaration of Helsinki.

miRNA Extraction

Total RNA was isolated from frozen macrodissected tissues or needle aspirates using the miRNeasy Mini Kit (Qiagen, Valencia, Calif., USA), according to the manufacturer protocol. The finale elution volume was 30 µL. RNA concentrations and purity were evaluated using NanoDrop 1000 Spectrophotometer (Wilmington, Del., USA) and RNA quality was determined by Bioanalyzer 2100 (Agilent, CA, USA).

Genome-Wide miRNA Profiling by Next Generation Sequencing (NGS)

The starting amount was 1 µg of total RNA, and the preparation protocol was performed according to the manufacturer's recommendations. Small RNA was isolated from total RNA on a 15% Novex TBE-Urea PAGE gel. The area representing band size of 18-30 nucleotides (nt) was cut out and fragmented, RNA was eluted in 0.3 M NaCl and purified on a Spin X column. The 5'-adapter was ligated for 6 hours at 20° C. Small RNA with ligated 5'-adapter was isolated on a 15% Novex TBE-Urea PAGE gel (Invitrogen, CA, USA). The 40-60 nt band was cut out and fragmented, RNA was eluted in 0.3 M NaCl and purified on a Spin X column. The 3'-adapter was ligated for 6 hours at 20° C. Small RNAs with ligated 5'- and 3"-adapters were isolated on a 10% Novex TBE-Urea PAGE gel, the 70-90 nt band was cut out and fragmented, RNA was eluted in 0.3 M NaCl and cleaned on a Spin X column. Then GlycoBlue and ethanol were added followed by precipitation for 30 minutes at −80° C. and centrifugation at 14000 rpm for 25 minutes. The RNA pellet was dissolved in 4.5 µl RNase free water. Reverse transcription and amplification was carried out and the cDNA was separated on a 6% Novex TBE PAGE gel. The amplified cDNA band was cut out and fragmented; RNA was eluted in Gel Elution Buffer and purified on a Spin X column. Then glycogen and ethanol were added for precipitation followed by centrifugation at 14 000 rpm and 4° C. for 20 minutes. The cDNA pellet was dissolved in 10 µl Resuspension Buffer. The cDNA library generated was evaluated with a quantitative real-time PCR to ensure acceptable quality and confirm that adapters were correctly added. The high-throughput sequencing of the cDNA was done in a 38 bp single-end read run on an Illumina Genome Analyzer IIx (Illumina, CA, USA). Image analysis and base calling was performed with the Illumina GA pipeline software version 1.5.1. Sequences with chastity less than 0.6 on two or more bases among the first 25 bases were filtered out.

Analysis of miRNA Expression by Real-Time qRT-PCR

The expression of the most discriminating miRNAs identified in the high-throughput sequencing was assessed by singleplex qRT-PCR using TaqMan miRNA Assays (Applied Biosystems Inc., Foster City, Calif., USA). A two-step protocol involves reverse transcription with a miRNA-specific primer, followed by a real time PCR with TaqMan probes. Briefly, 5 ng total RNA was used per reverse transcription reaction performed in final volume of 7.5 µL (2.5 µL RNA, 0.075 µL of 100 mM dNTPs, 0.5 µL of Multiscribe Reverse Transcriptase (50U µL-1), 0.75 µL of 10×RT buffer, 0.095 µL of RNase inhibitor (20U µL-1), stemloop RT primer and 2.084, Nuclease-free water) and incubated for: 30 minutes, 16° C.; 30 minutes, 42° C.; 5 minutes, 85° C.; hold at 4° C. The 10 μL PCR mixture included 2 μL cDNA, 5 μL of TaqMan 2× Universal PCR Master Mix with no AmpErase UNG and 0.5 μL of TaqMan 20× MicroRNA Assay. PCR reactions were incubated in a 384-well optical plate and run on the Viia7 Real-Time PCR System (Applied Biosystems Inc.) as follows: 95° C. for 10 min and 50 cycles of 95° C. for 15 sec and 60° C. for 1 min. All specimens were amplified in duplicates.

Amplification data was normalized against RNU6B as endogenous control. Ct values were calculated from automatic threshold. No template controls showed any amplification. Relative expression levels of selected miRNAs were calculated for each sample as −Δct values [−ΔCt=−(Ct of target miRNA −Ct of endogenous control miRNA)].

Data Analysis

Data from the high-throughput sequencing was obtained in FASTQ format, one data file per sequencing lane. The sequencing adaptors were subsequently clipped and removed using the FASTX-Toolkit, allowing no mismatches for adaptor identification. The remaining sequencing data was further collapsed and counted into groups of identical sequences. The sequencing data was further processed to identify miRs from the miRBase (release 18) data repository. It also evaluates sequence alignment to other entities through the databases RefSeq and Rfam. Sequence data was aligned to the *Homo Sapiens* hg18 genome reference allowing for one mismatch. Differential expression (DE) of identified miRs from miRBase was calculated with R version 2.13.0 using DESeq package 1.4.1 available in Bioconductor version 2.8. The count data was normalized to the estimated size factors and differential expression (fold change) of known miRs was analyzed between groups, as the ratio between normalized count data for tumor and normal samples. P-values are adjusted for multiple testing using the Benjamini and Hochberg method. Only miRs with a fold change with adjusted P-value with false discovery rate (FDR)<0.05 are considered significant.

Example 1. MiRNA Expression Profile Analyzed by NGS Discriminates Between IPMN, PDAC and Normal Pancreas Overview A flow diagram of the study design is given in FIG. 1. This is one of the first studies to investigate the miRNA expression profile in PDAC and IPMN using next-generation sequencing. The study was conducted in 2 main steps: a genome-wide miRNA profiling to discover new potential biomarkers and a validation of the most significant results by qRT-PCR in two independent groups of samples. We focused on those miRNA commonly deregulated in both IPMN and PDAC with the aim of finding good candidate biomarkers for detection of both neoplastic lesions, due to the high risk of malignancy that IPMN lesions have.

Results

Figure 2:
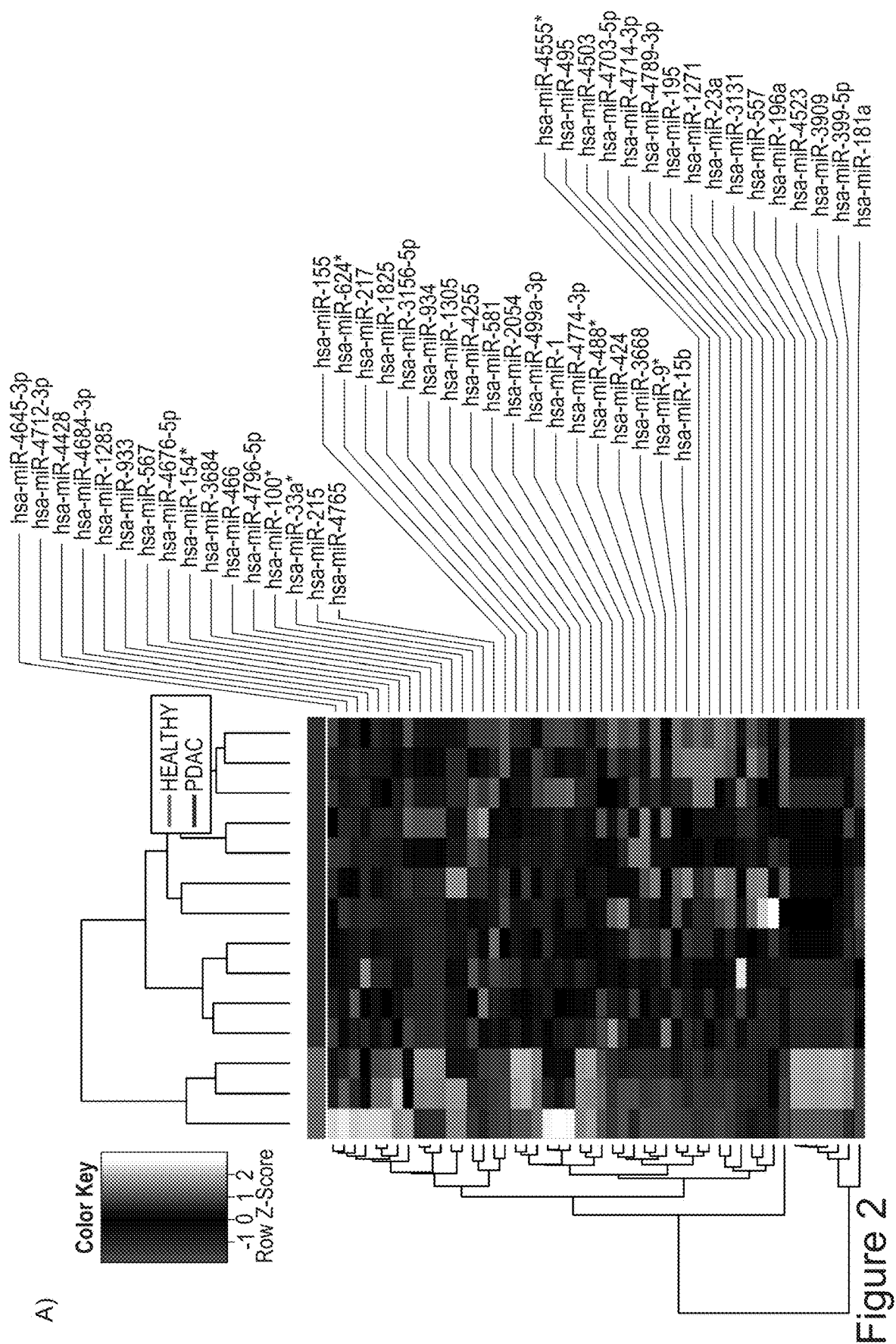
FIG. 2. Next generation sequencing results. A) PDAC vs HEALTHY. Heatmap TOP 50 B) IPMN vs HEALTHY. Heatmap TOP 50. C) Between group analysis showing sample clustering based on miRNA expression.
Figure 2:
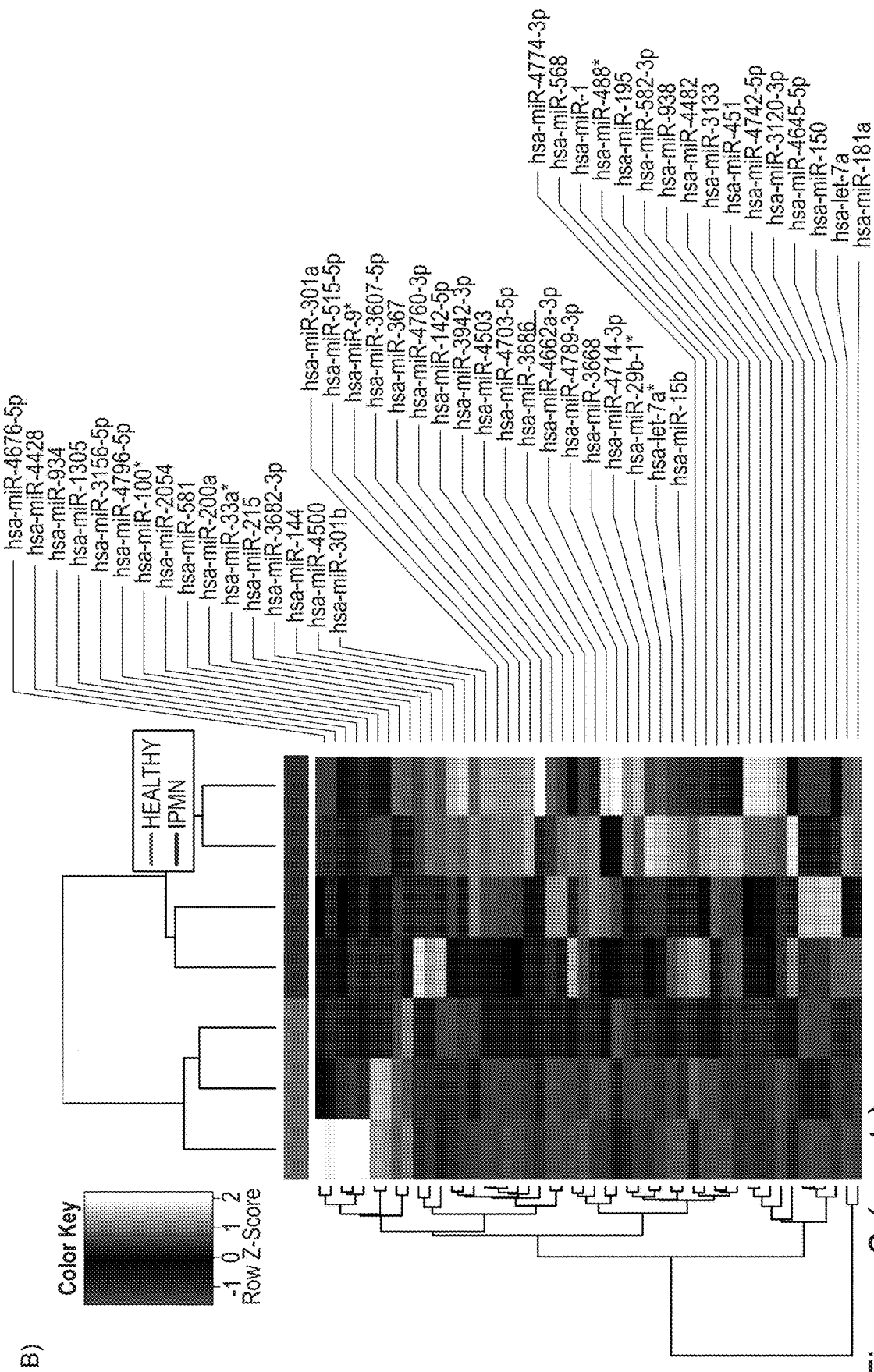
Figure 2:
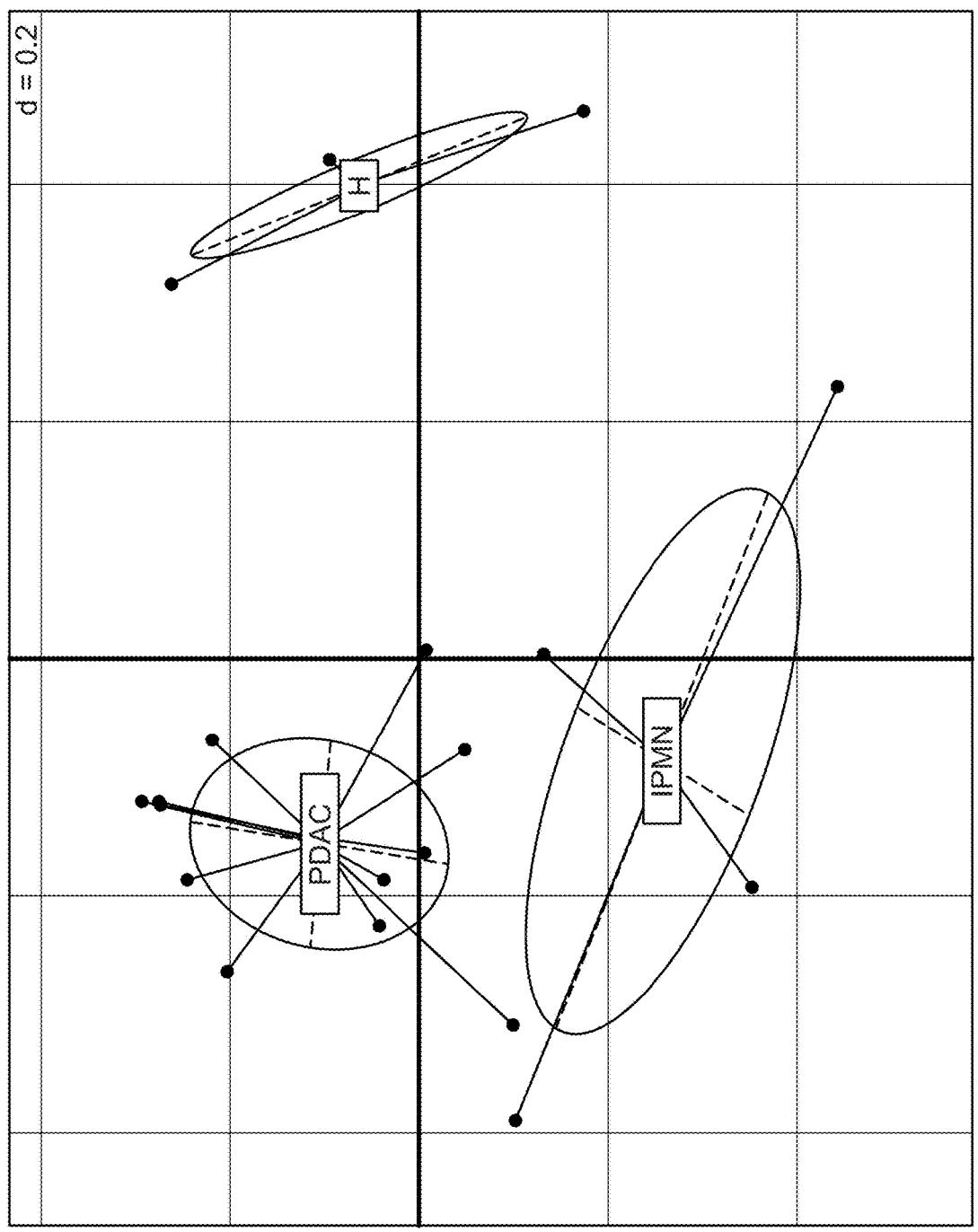

We first analyzed the miRNome of 11 PDAC, 4 IPMN and 3 healthy pancreatic tissues using the Genome Analyzer (Illumina). By performing the next-generation sequencing technique, we found a total of 1733 miRNAs represented in the 18 samples. Expression profiles of the 50 miRNAs with the highest significant fold-change between PDAC patients and healthy individuals are depicted in FIG. 2A and the 50 most significantly deregulated in IPMN versus healthy pancreas are represented in FIG. 2B. BGA graph was then performed to visually represent the proximity between patients suffering from PDAC or IPMN and controls, according to miRNA expression. As shown in FIG. 2C, miRNA expression profiles of NGS-sequenced samples can classify between PDAC, IPMN and healthy groups.

Figure 3:
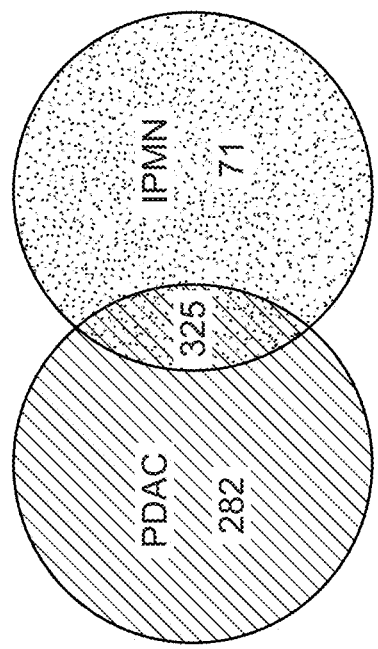
FIG. 3. PDAC and IPMN specimens share common deregulated microRNAs. A) Venn diagram showing significantly deregulated miRNAs among the PDAC and IPMN groups compared with normal pancreatic samples (healthy group). B) Volcano plot of NGS data. Green: miRNA commonly deregulated in PDAC and IPMN groups (FDR<0.05). Dark green: miRNA strongly upregulated (FC>2, FDR<0.05 and mean counts across all samples>400) in PDAC and IPMN groups. Orange crosses: miRNA selected for validation by qRT-PCR in a training set.
Figure 3:
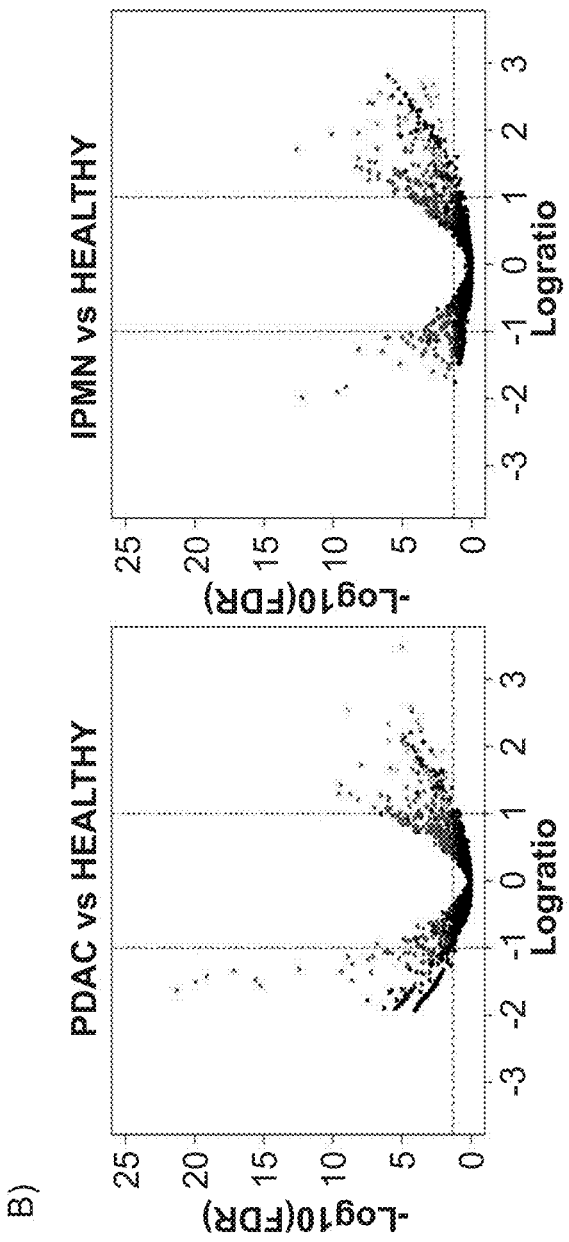

Employing the DESeq package for an initial comparative analysis, we found 607 and 396 miRNAs significantly deregulated (FDR<0.05) in PDAC and IPMN samples when compared to healthy controls, respectively. In addition, both PDAC and IPMN shared 325 miRNAs significantly deregulated (FIG. 3A). Of this commonly deregulated miRNAs, there were 107 miRNAs who had a fold change more than 2 and mean counts over 400. Next, to select a group of miRNAs to carry out further experimental validation, we took into account those miRNAs with a maximum interquartile range logarithm of 1.4 to ensure selecting those miRNAs showing less dispersion intra-group. A total of 40 miRNAs met all the criteria mentioned above (FDR<0.05, FC>2, mean counts>400 and intragroup IQR log ⇐1.4) and were commonly upregulated in PDAC and IPMN (Table 5). The volcano plot of NGS data in FIG. 3B graphically depicts these results of the differential miRNA expression analysis. In conclusion, the NGS data resulted in the identification of several miRNAs capable of discriminating the pre-malignant lesion IPMN from healthy pancreas, PDAC tissue from healthy pancreas and also between IPMN and PDAC.

Example 2. Validation of Tissue-Based miRNA Expression by qRT-PCR Reproduced Most of the NGS Results To confirm the NGS results, we first analyzed the expression of the 40 selected miRNAs by using TaqMan qRT-PCR in 52 samples from the training set (24 PDAC, 7 IPMN, 6 CP, 15H). We were able to validate upregulation of 31 miRNAs (23 with p<0.05 and 8 with p<0.1) in PDAC samples and 24 miRNAs were also upregulated in IPMN samples (18 with p<0.05, and 6 with p<0.1) (Table 2).

Figure 4:
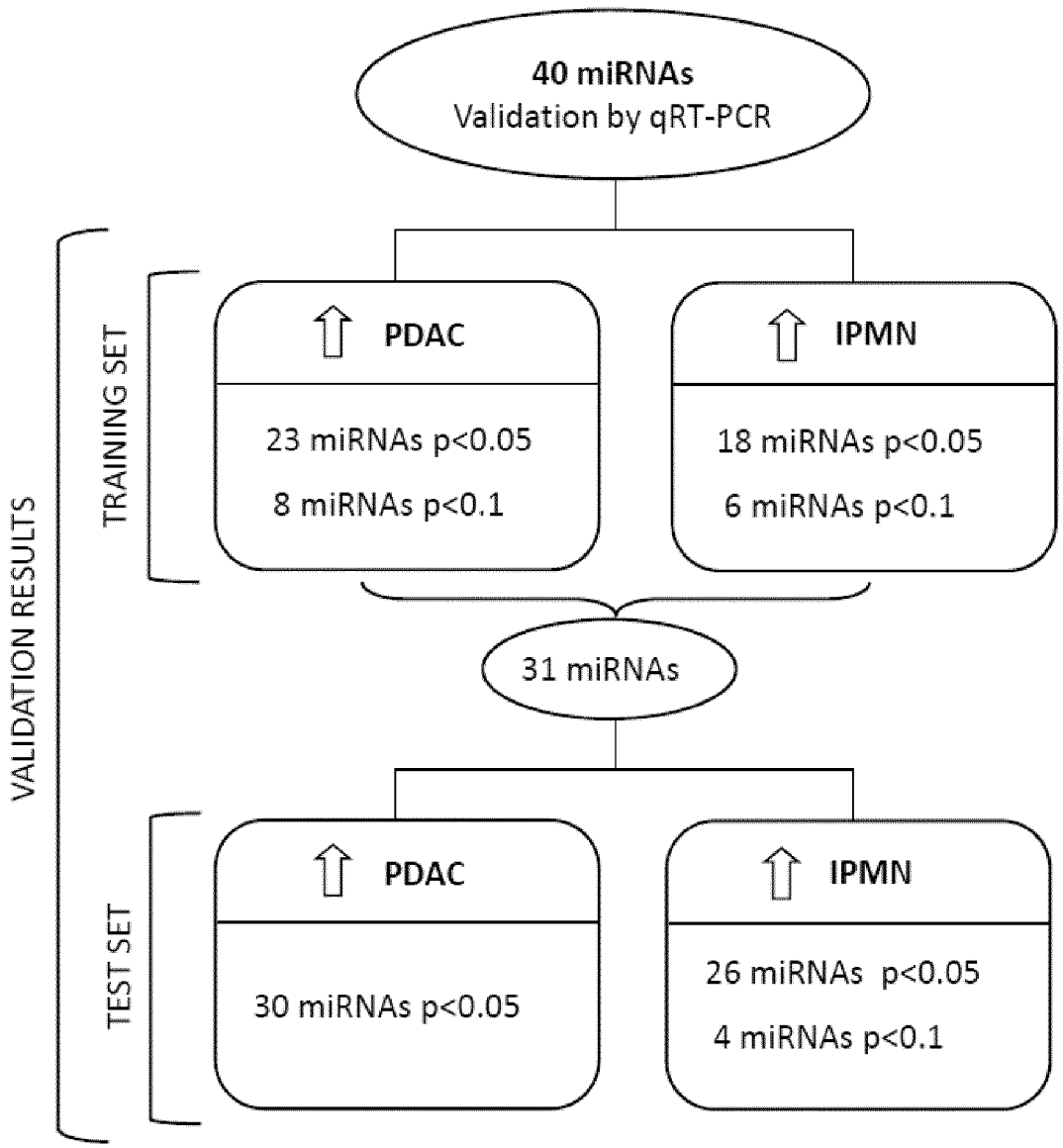
FIG. 4. Workflow of study results. Number of miRNAs significantly overexpressed in PDAC and IPMN samples versus healthy pancreatic tissue in two independent set of samples.

None of the 40 miRNAs analyzed by qRT-PCR showed a significant difference in expression between the chronic pancreatitis tissue analyzed and healthy pancreas (data not shown). Next, in order to corroborate the previous results, we employed qRT-PCR to further investigate the expression of 31 miRNAs validated in the training set in another independent set of 95 EUS-FNA pancreatic samples (test set). We confirmed the expression pattern of 30 miRNAs that were significantly upregulated (30 with p<0.05) in 60 patients with PDAC when compared with 26 healthy controls. Concerning the IPMN group (n=9), we validated 30 miRNAs as being overexpressed (26 with p<0.05 and 4 with p<0.1) in comparison with the healthy group (n=26). The results from these experiments are shown in table 5 and schematized in FIG. 4.

Overall, qRT-PCR analysis in 2 different cohorts confirmed most of the NGS results. We identified and validated 30 miRNAs whose expression is significantly increased in PDAC and IPMN lesions.

Figure 5:
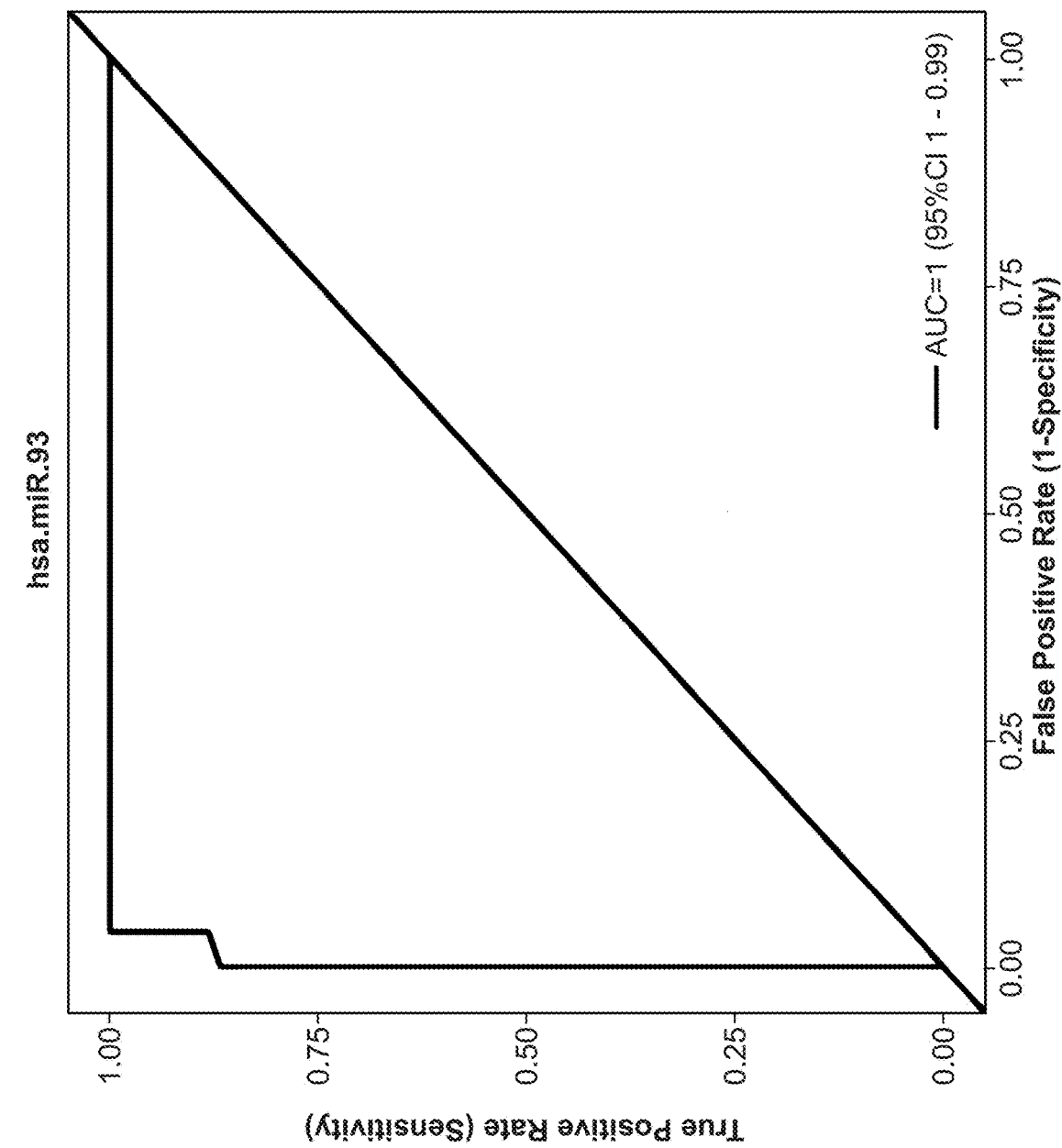
FIG. 5. Receiver operating characteristic (ROC) curves of 8 miRNAs illustrating high discriminatory power for PDAC patients.
Figure 5:
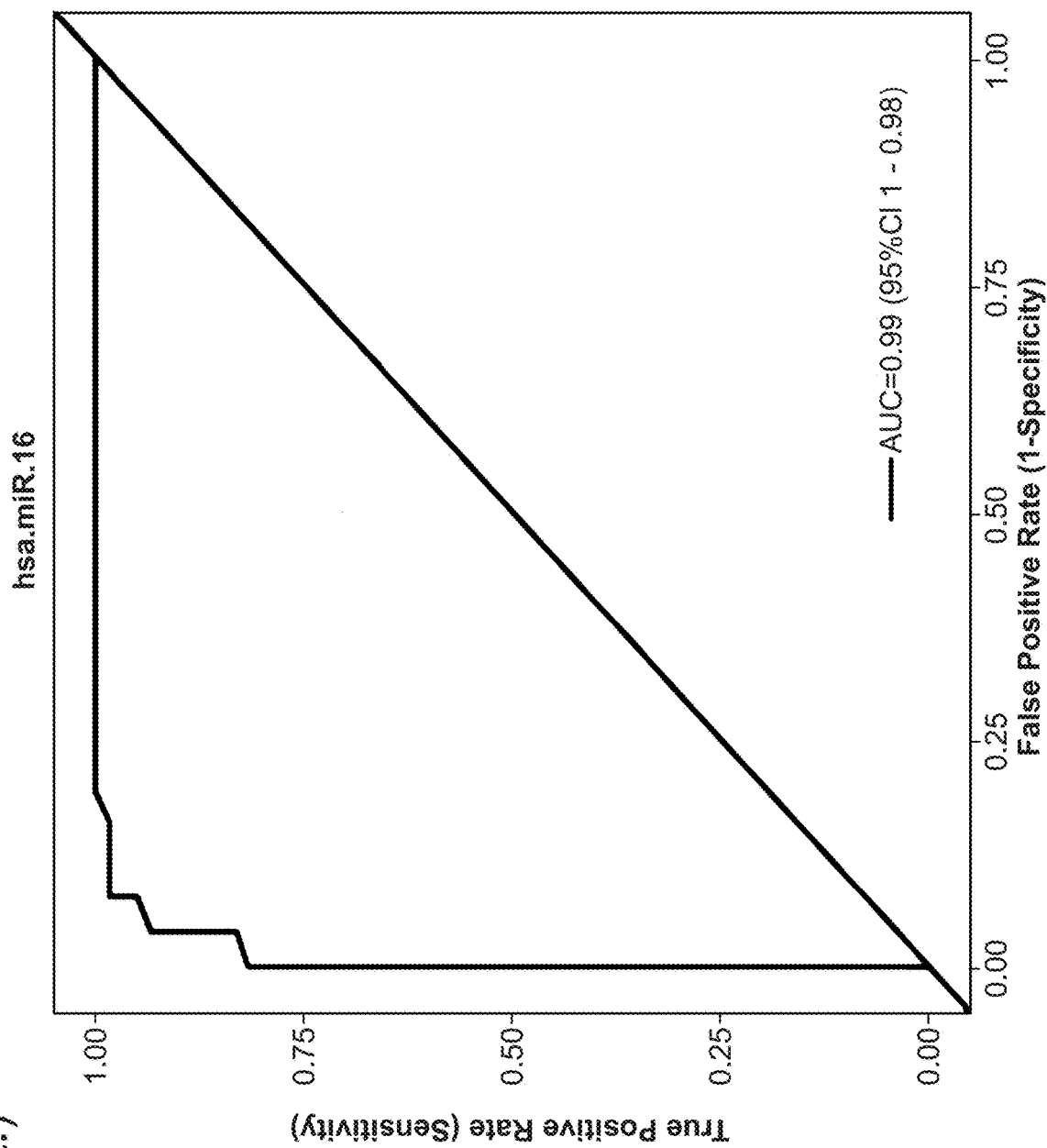
Figure 5:
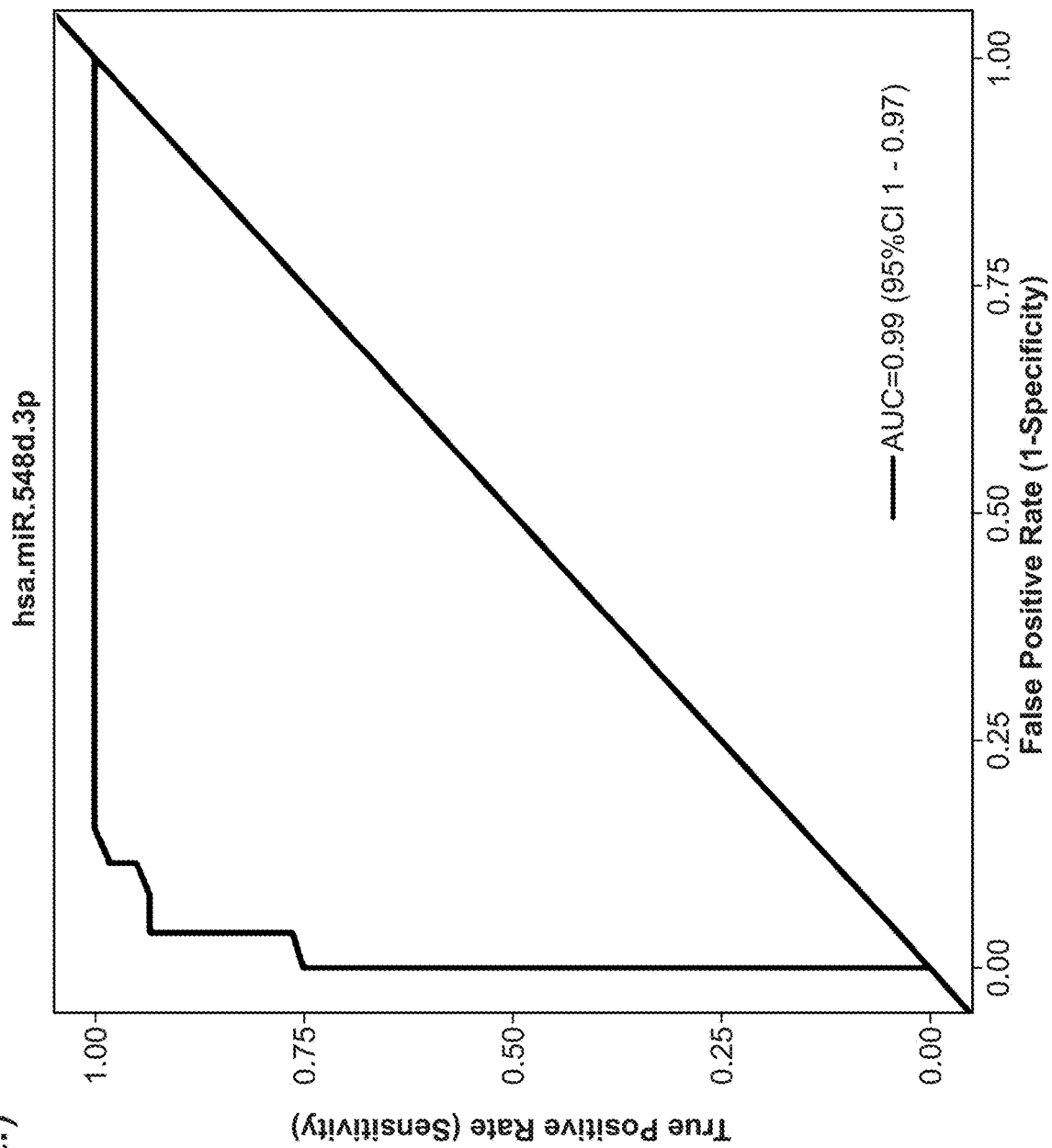
Figure 5:
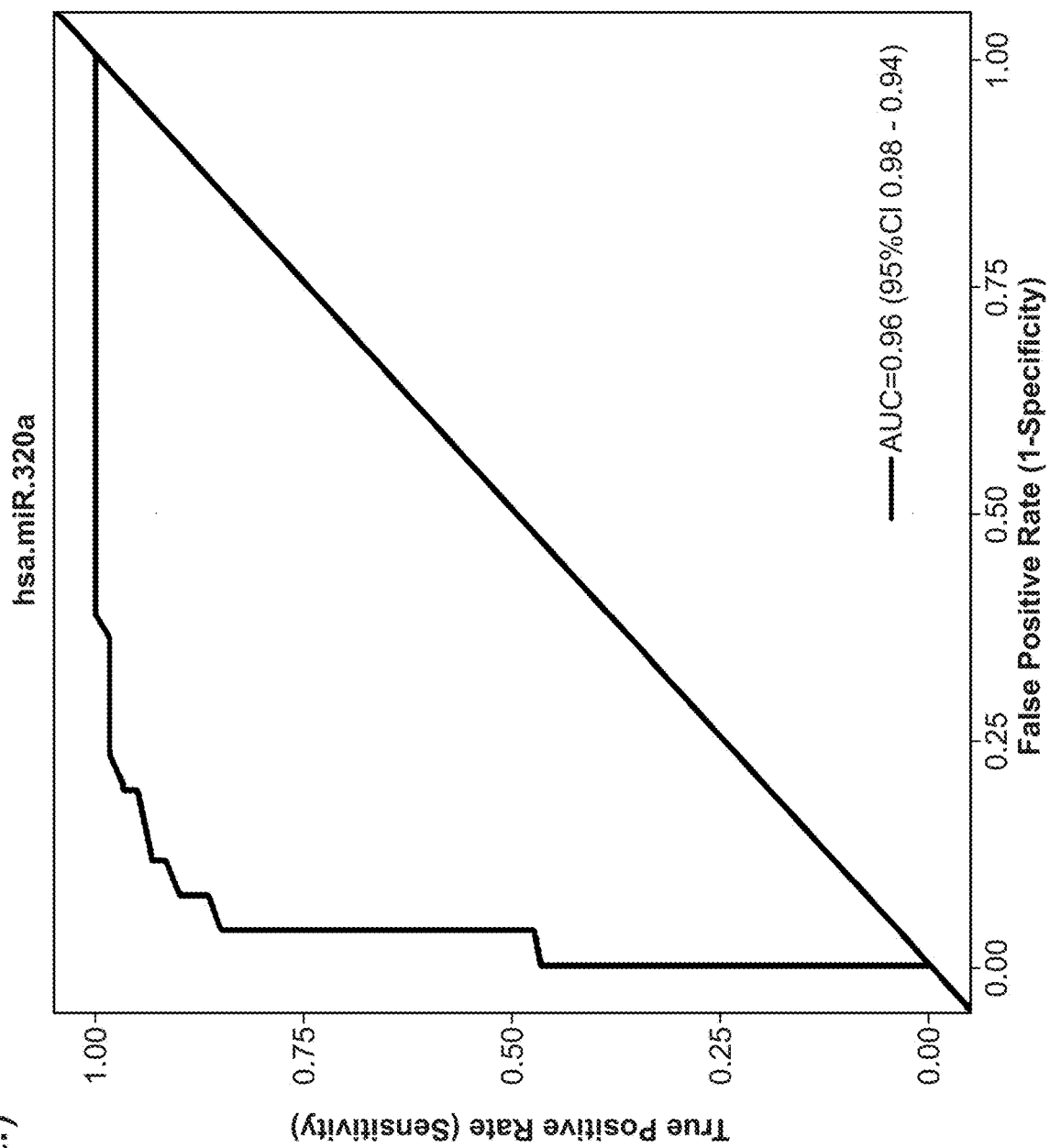
Figure 5:
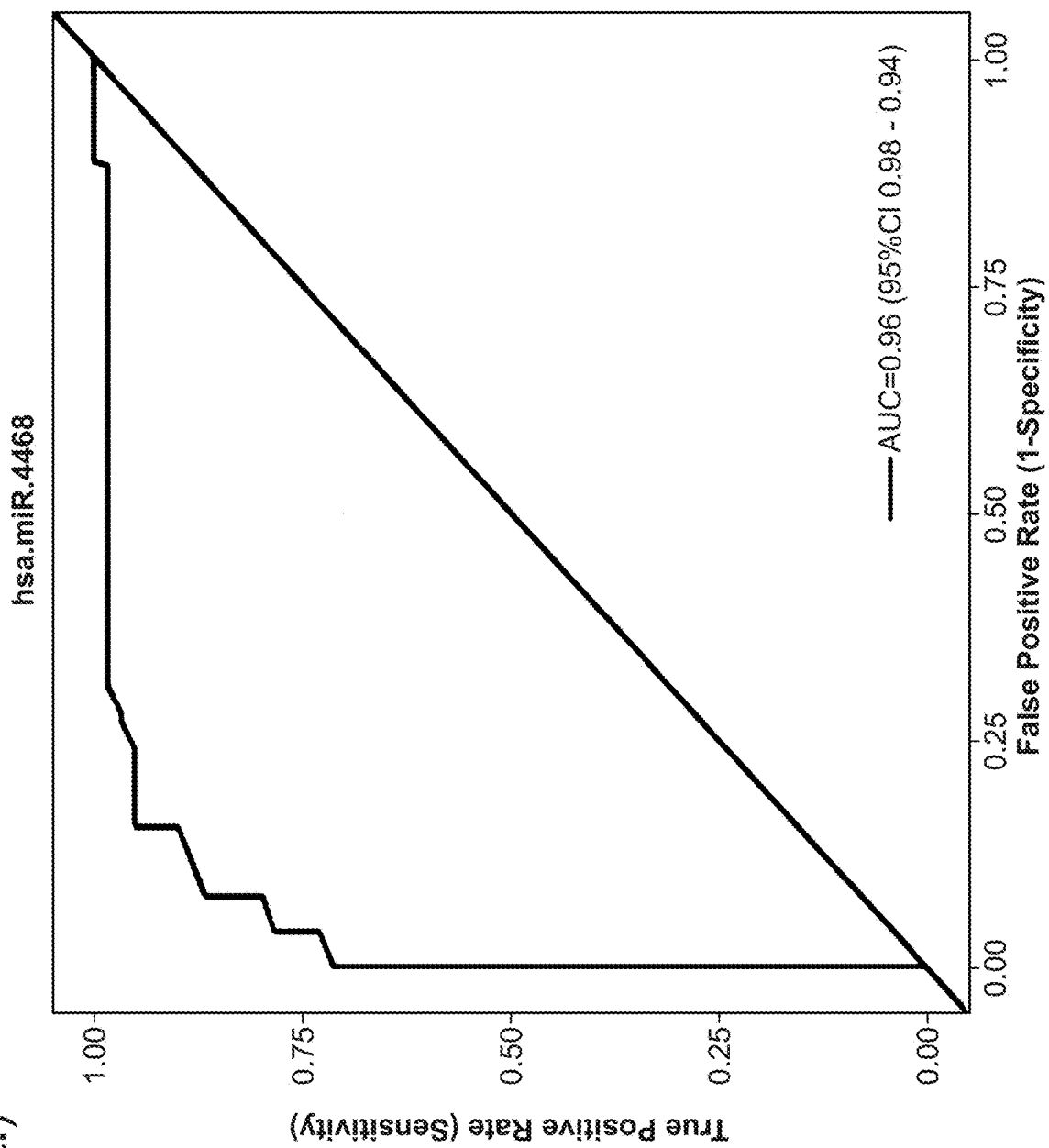
Figure 5:
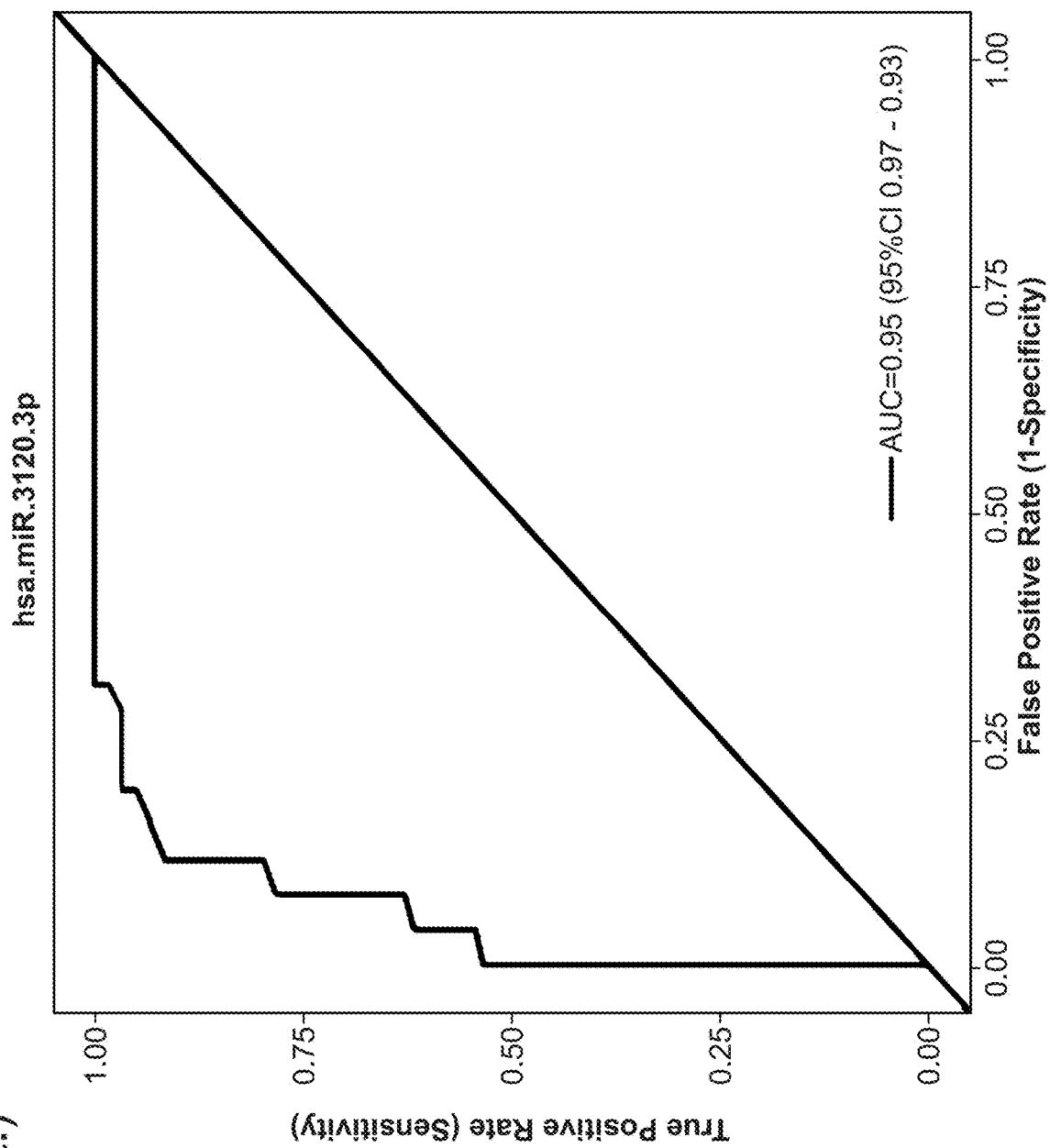
Figure 5:
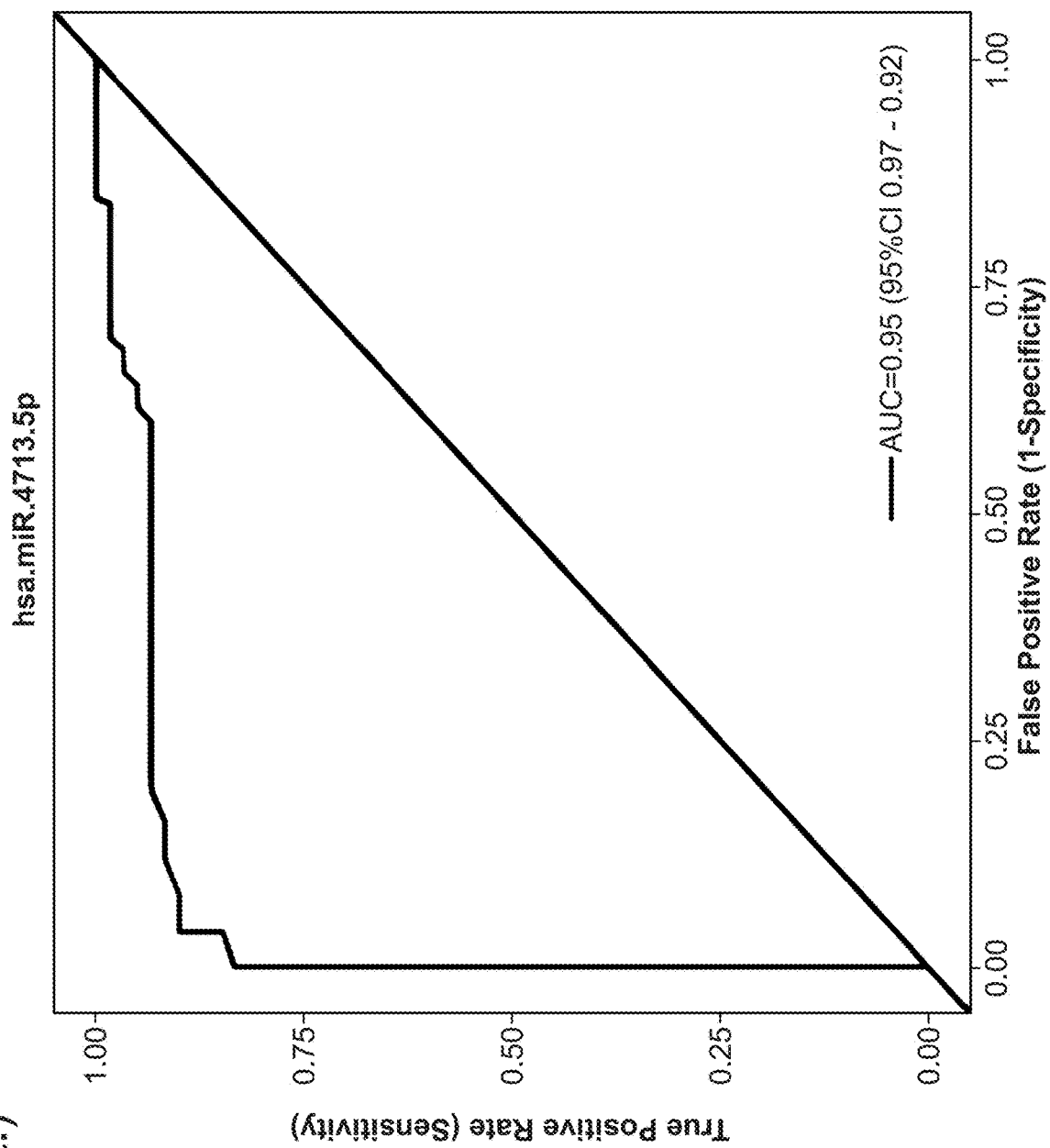
Figure 5:
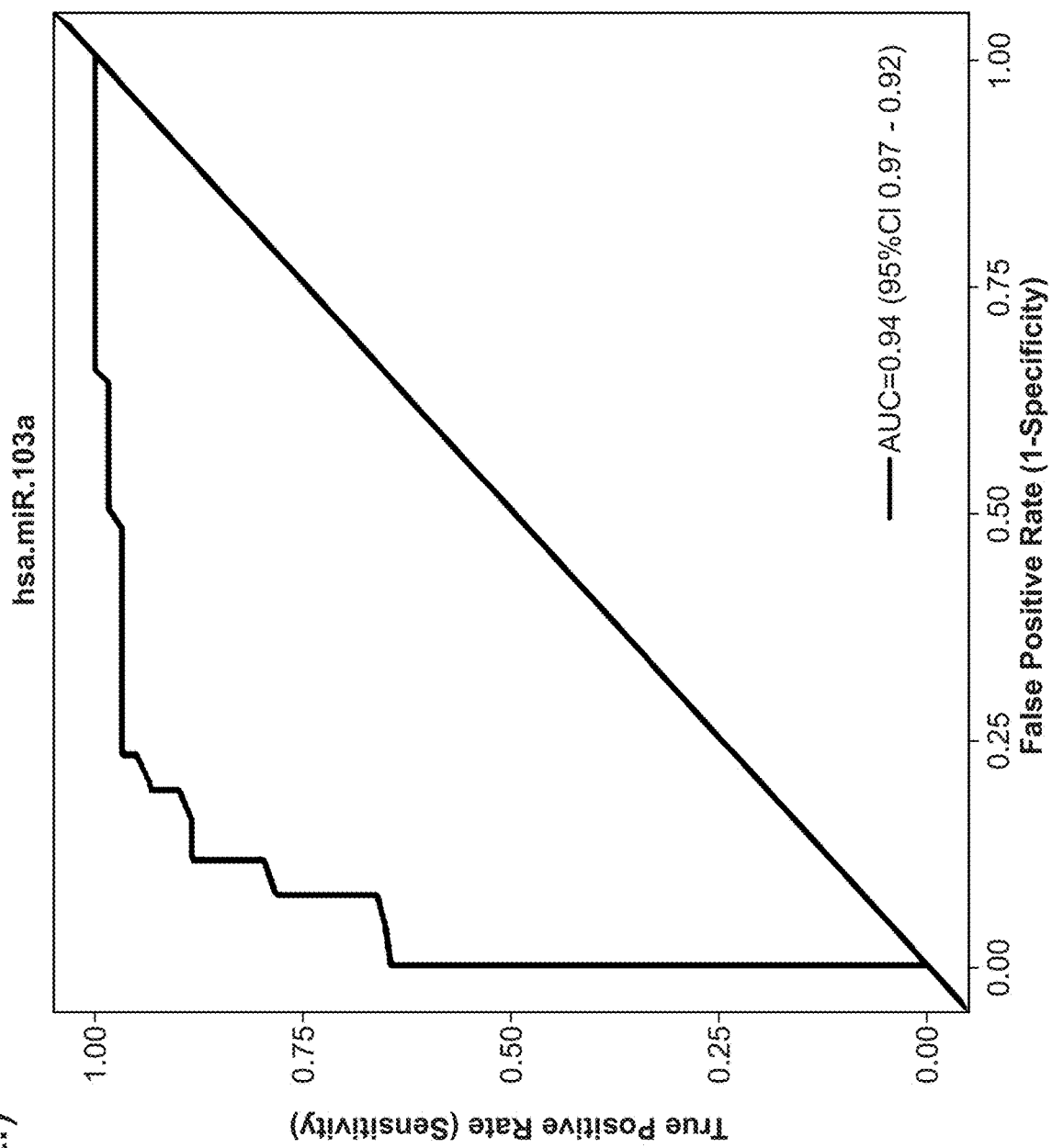

Example 3. Several miRNAs Validated in the Test Set Show High Accuracy to Discriminate Between Patients with PDAC and Controls Regarding the discriminatory capacity to distinguish PDAC patients from controls, the 30 miRNAs validated in the test set presented areas under ROC curve (AUC) ranging from 0.69 (95% CI: 0.75-0.64) to 1 (95% CI: 1-0.99). Specifically, 13 of these 30 miRNAs (miR-93, miR-16, miR-548d-3p, miR-320a, miR-4468, miR-3120-3p, miR-4713-5p, miR-103a, miR-155, miR-4770, miR-181a, miR-221 and miR-151b) demonstrated a high accuracy in discriminating PDAC patients from healthy controls with an AUC over 0.9 (table 3). FIG. 5 shows ROC curves of 8 miRNAs with the highest discriminative capacity for PDAC patients. Finally, it is worth highlighting the performance of miR-93, which is a single tissue-based miRNA significantly altered in PDAC with an excellent sensitivity and specificity to differentiate cancerous tissue from normal pancreas.

TABLE 5

List of 40 highly discriminating microRNAs between PDAC or IPMN and healthy tissues. MicroRNAs selected from NGS data and their values obtained in subsequent validaton phases.

| | Discovery Phase (NGS) | | | | Training set (qRT-PCR) | |
|---|---|---|---|---|---|---|
| microRNA | FC PDAC vs H | FDR PDAC vs H | FC IPMN vs H | FDR IPMN vs H | FC PDAC vs H | FDR PDAC vs H |
| hsa-let-7c | 3.80 | 9.1E−03 | 6.37 | 1.8E−03 | 2.09 | 8.1E−02 |
| hsa-let-7e | 4.08 | 1.5E−05 | 3.97 | 3.1E−04 | 2.33 | 1.1E−02 |
| hsa-let-7f | 2.89 | 1.3E−02 | 5.58 | 6.3E−04 | 2.86 | 9.2E−03 |
| hsa-miR-103a | 2.80 | 2.3E−03 | 3.13 | 4.8E−03 | 6.21 | 3.8E−03 |
| hsa-miR-1257 | 3.03 | 5.4E−04 | 3.02 | 3.7E−03 | 3.51 | 2.3E−02 |
| hsa-miR-1304 | 5.12 | 1.2E−04 | 5.54 | 7.1E−04 | 1.81 | 1.1E−01 |
| hsa-miR-151a-5p | 2.10 | 1.6E−02 | 3.05 | 2.5E−03 | 2.99 | 5.2E−03 |
| hsa-miR-151b | 2.25 | 8.5E−03 | 3.27 | 1.2E−03 | 2.87 | 9.1E−03 |
| hsa-miR-155 | 4.25 | 1.1E−06 | 3.67 | 3.3E−04 | 11.80 | 3.3E−03 |
| hsa-miR-16 | 2.06 | 1.5E−02 | 2.83 | 5.0E−03 | 4.86 | 9.7E−03 |
| hsa-miR-181a | 5.83 | 1.2E−09 | 5.88 | 2.5E−07 | 8.00 | 5.0E−03 |
| hsa-miR-181b | 3.00 | 8.2E−04 | 2.66 | 1.4E−02 | 41.51 | 9.9E−03 |
| hsa-miR-192 | 3.11 | 1.5E−02 | 4.41 | 5.8E−03 | 1.79 | 1.7E−01 |
| hsa-miR-21 | 11.18 | 9.8E−06 | 5.70 | 3.3E−03 | 7.84 | 8.9E−04 |
| hsa-miR-221 | 3.62 | 2.3E−03 | 4.04 | 6.0E−03 | 4.09 | 2.5E−03 |
| hsa-miR-23a | 5.03 | 1.0E−06 | 4.79 | 3.6E−05 | 4.25 | 4.9E−03 |
| hsa-miR-29a | 2.14 | 1.3E−02 | 3.44 | 7.8E−04 | 2.54 | 5.4E−03 |
| hsa-miR-3120-3p | 4.49 | 1.2E−05 | 6.68 | 2.2E−06 | 4.75 | 3.4E−02 |
| hsa-miR-3133 | 3.80 | 2.7E−05 | 5.56 | 1.2E−06 | 1.79 | 7.4E−02 |
| hsa-miR-3145-3p | 5.90 | 5.0E−05 | 6.33 | 3.6E−04 | −1.64 | 7.3E−01 |
| hsa-miR-320a | 2.37 | 1.6E−02 | 2.55 | 3.7E−02 | 7.65 | 4.7E−03 |
| hsa-miR-33a* | 3.14 | 4.5E−06 | 4.26 | 1.5E−07 | 1.84 | 4.6E−02 |
| hsa-miR-3692 | 3.41 | 9.7E−05 | 4.49 | 1.8E−05 | 1.79 | 4.9E−01 |
| hsa-miR-3714 | 2.49 | 4.1E−03 | 2.66 | 9.1E−03 | 1.76 | 5.4E−02 |
| hsa-miR-4256 | 2.85 | 9.2E−04 | 2.78 | 6.2E−03 | −2.03 | 4.5E−01 |
| hsa-miR-429 | 2.47 | 6.7E−03 | 2.70 | 4.6E−03 | 2.13 | 5.8E−02 |
| hsa-miR-4313 | 2.18 | 1.2E−02 | 2.18 | 3.9E−02 | −1.20 | 6.0E−01 |
| hsa-miR-4468 | 4.77 | 2.4E−04 | 5.15 | 1.5E−03 | 3.21 | 4.5E−02 |
| hsa-miR-4639-5p | 5.08 | 1.3E−04 | 5.45 | 9.5E−04 | 3.13 | 4.7E−02 |
| hsa-miR-4642 | 2.83 | 9.8E−04 | 3.02 | 2.9E−03 | −1.06 | 9.0E−01 |
| hsa-miR-4666-3p | 3.10 | 8.9E−05 | 2.34 | 1.4E−02 | −1.01 | 9.2E−01 |
| hsa-miR-4713-5p | 3.84 | 1.6E−04 | 5.42 | 6.9E−05 | 2.19 | 9.2E−02 |
| hsa-miR-4714-5p | 3.14 | 4.8E−04 | 2.96 | 5.2E−03 | 5.31 | 4.5E−02 |
| hsa-miR-4723-5p | 5.23 | 1.3E−04 | 5.56 | 9.5E−04 | 1.83 | 2.9E−01 |
| hsa-miR-4770 | 5.99 | 3.9E−05 | 6.43 | 3.0E−04 | 1.68 | 9.2E−02 |
| hsa-miR-4801 | 2.22 | 1.5E−02 | 2.29 | 2.6E−02 | 1.70 | 1.6E−01 |
| hsa-miR-548d-3p | 2.44 | 1.1E−02 | 2.16 | 4.0E−02 | 8.16 | 1.2E−02 |
| hsa-miR-616* | 2.84 | 1.7E−03 | 2.98 | 2.4E−03 | 1.39 | 1.9E−01 |
| hsa-miR-761 | 2.00 | 6.2E−03 | 2.07 | 1.3E−02 | 2.19 | 8.8E−02 |
| hsa-miR-93 | 2.75 | 1.4E−03 | 3.90 | 2.0E−04 | 6.59 | 5.9E−03 |

| | Training set (qRT-PCR) | | Test set (qRT-PCR) | | | |
|---|---|---|---|---|---|---|
| microRNA | FC IPMN vs H | FDR IPMN vs H | FCPDAC vs H | FDR PDAC vs H | FC IPMN vs H | FDR IPMN vs H |
| hsa-let-7c | 2.87 | 2.0E−02 | −1.10 | 1.4E−01 | 3.45 | 2.5E−03 |
| hsa-let-7e | 2.55 | 2.9E−02 | 3.94 | 4.5E−06 | 5.06 | 2.0E−03 |
| hsa-let-7f | 3.61 | 2.8E−02 | 6.72 | 1.0E−07 | 6.21 | 1.1E−03 |
| hsa-miR-103a | 5.49 | 2.3E−02 | 31.36 | 1.0E−10 | 20.06 | 2.5E−04 |
| hsa-miR-1257 | 2.08 | 3.3E−01 | 23.13 | 5.8E−07 | 4.30 | 4.7E−02 |
| hsa-miR-1304 | 1.71 | 2.9E−01 | 6.36 | 2.3E−07 | 4.24 | 3.8E−02 |
| hsa-miR-151a-5p | 3.49 | 1.8E−02 | 5.47 | 1.5E−08 | 5.28 | 1.5E−03 |
| hsa-miR-151b | 3.70 | 2.4E−02 | 6.81 | 1.9E−09 | 5.28 | 9.8E−04 |
| hsa-miR-155 | 5.37 | 2.5E−02 | 14.49 | 4.7E−10 | 10.62 | 2.7E−04 |
| hsa-miR-16 | 5.14 | 6.4E−02 | 79.68 | 6.2E−13 | 17.78 | 7.8E−04 |
| hsa-miR-181a | 6.69 | 1.6E−02 | 7.09 | 3.8E−10 | 5.77 | 2.2E−04 |
| hsa-miR-181b | 88.28 | 5.1E−02 | 4.57 | 2.1E−08 | 4.82 | 3.3E−04 |
| hsa-miR-192 | 4.64 | 2.6E−02 | 8.37 | 2.5E−08 | 4.51 | 1.6E−02 |
| hsa-miR-21 | 4.61 | 2.5E−02 | 10.20 | 5.5E−09 | 8.35 | 9.2E−04 |
| hsa-miR-221 | 3.23 | 3.7E−02 | 6.56 | 1.5E−09 | 5.38 | 2.3E−03 |
| hsa-miR-23a | 2.67 | 3.7E−02 | 4.79 | 5.5E−04 | 6.07 | 5.9E−04 |
| hsa-miR-29a | 2.67 | 3.5E−02 | 2.19 | 1.9E−03 | 2.91 | 8.4E−03 |
| hsa-miR-3120-3p | 4.91 | 9.2E−02 | 99.28 | 3.3E−11 | 5.22 | 7.3E−02 |
| hsa-miR-3133 | 3.22 | 1.0E−01 | 3.51 | 5.9E−06 | 1.43 | 7.8E−02 |
| hsa-miR-3145-3p | 1.27 | 7.0E−01 | n/a | n/a | n/a | n/a |
| hsa-miR-320a | 9.03 | 2.4E−02 | 11.40 | 1.3E−11 | 7.52 | 1.2E−03 |
| hsa-miR-33a* | 2.46 | 3.6E−02 | 5.04 | 1.4E−06 | 5.14 | 3.1E−03 |
| hsa-miR-3692 | 3.97 | 1.3E−01 | n/a | n/a | n/a | n/a |
| hsa-miR-3714 | −1.07 | 9.1E−01 | 3.58 | 2.0E−06 | 1.03 | 2.0E−01 |
| hsa-miR-4256 | −1.30 | 8.2E−01 | n/a | n/a | n/a | n/a |

TABLE 5-continued

List of 40 highly discriminating microRNAs between PDAC or
IPMN and healthy tissues. MicroRNAs selected from NGS data
and their values obtained in subsequent validaton phases.

| | | | | | | |
|---|---|---|---|---|---|---|
| hsa-miR-429 | 4.82 | 3.6E−02 | 3.80 | 6.0E−05 | 5.12 | 7.0E−03 |
| hsa-miR-4313 | 1.00 | 9.7E−01 | n/a | n/a | n/a | n/a |
| hsa-miR-4468 | 1.77 | 2.6E−01 | 29.64 | 2.7E−11 | 1.85 | 1.1E−01 |
| hsa-miR-4639-5p | 2.81 | 6.9E−02 | 71.10 | 6.5E−07 | 43.92 | 3.7E−03 |
| hsa-miR-4642 | −1.05 | 9.5E−01 | n/a | n/a | n/a | n/a |
| hsa-miR-4666-3p | −1.58 | 1.9E−01 | n/a | n/a | n/a | n/a |
| hsa-miR-4713-5p | −1.69 | 6.3E−01 | 26.29 | 5.4E−11 | 2.51 | 1.1E−01 |
| hsa-miR-4714-5p | 3.19 | 5.8E−01 | 20.42 | 4.8E−03 | 3.00 | 3.6E−02 |
| hsa-miR-4723-5p | 1.67 | 1.6E−01 | n/a | n/a | n/a | n/a |
| hsa-miR-4770 | −1.01 | 8.8E−01 | 10.49 | 4.7E−10 | 4.88 | 7.7E−03 |
| hsa-miR-4801 | 1.63 | 3.1E−01 | n/a | n/a | n/a | n/a |
| hsa-miR-548d-3p | 3.84 | 2.2E−01 | 419.19 | 1.1E−12 | 36.48 | 2.5E−03 |
| hsa-miR-616* | 1.52 | 1.3E−01 | n/a | n/a | n/a | n/a |
| hsa-miR-761 | 3.73 | 5.9E−02 | 3.13 | 1.4E−03 | 2.74 | 3.5E−02 |
| hsa-miR-93 | 5.25 | 3.9E−02 | 77.77 | 3.8E−13 | 19.10 | 3.5E−04 |

TABLE 6

Receiver operating characteristics (ROC) curve analysis of all miRNAs analyzed in the test set.

| | AUC (PDAC vs H) | 95% CI | p-value | AUC (IPMN vs H) | 95% CI | p-value |
|---|---|---|---|---|---|---|
| hsa-miR-93 | 0.995 | 1.001-0.989 | 3.78E−13 | 0.905 | 0.973-0.837 | 3.46E−04 |
| hsa-miR-16 | 0.991 | 0.999-0.982 | 6.18E−13 | 0.881 | 0.955-0.806 | 7.77E−04 |
| hsa-miR-548d-3p | 0.985 | 0.996-0.974 | 1.08E−12 | 0.843 | 0.927-0.759 | 2.47E−03 |
| hsa-miR-320a | 0.961 | 0.980-0.943 | 1.31E−11 | 0.867 | 0.946-0.789 | 1.18E−03 |
| hsa-miR-4468 | 0.954 | 0.974-0.934 | 2.73E−11 | 0.682 | 0.788-0.577 | 1.07E−01 |
| hsa-miR-3120-3p | 0.952 | 0.973-0.932 | 3.28E−11 | 0.703 | 0.807-0.599 | 7.31E−02 |
| hsa-miR-4713-5p | 0.947 | 0.969-0.925 | 5.38E−11 | 0.682 | 0.788-0.576 | 1.08E−01 |
| hsa-miR-103a | 0.940 | 0.964-0.917 | 1.04E−10 | 0.914 | 0.979-0.850 | 2.53E−04 |
| hsa-miR-181a | 0.927 | 0.953-0.901 | 3.82E−10 | 0.919 | 0.982-0.855 | 2.18E−04 |
| hsa-miR-155 | 0.925 | 0.951-0.898 | 4.65E−10 | 0.912 | 0.978-0.847 | 2.70E−04 |
| hsa-miR-4770 | 0.925 | 0.951-0.898 | 4.69E−10 | 0.802 | 0.893-0.710 | 7.72E−03 |
| hsa-miR-221 | 0.912 | 0.941-0.883 | 1.53E−09 | 0.846 | 0.929-0.762 | 2.26E−03 |
| hsa-miR-151b | 0.910 | 0.939-0.880 | 1.87E−09 | 0.873 | 0.950-0.796 | 9.81E−04 |
| hsa-miR-21 | 0.897 | 0.929-0.866 | 5.52E−09 | 0.875 | 0.952-0.799 | 9.21E−04 |
| hsa-miR-151a-5p | 0.886 | 0.919-0.853 | 1.49E−08 | 0.860 | 0.940-0.780 | 1.48E−03 |
| hsa-miR-181b | 0.882 | 0.916-0.848 | 2.06E−08 | 0.907 | 0.974-0.840 | 3.25E−04 |
| hsa-miR-192 | 0.880 | 0.914-0.845 | 2.52E−08 | 0.772 | 0.868-0.676 | 1.63E−02 |
| hsa-miR-23a | 0.871 | 0.906-0.835 | 5.48E−08 | 0.889 | 0.962-0.816 | 5.92E−04 |
| hsa-miR-let-7f | 0.863 | 0.900-0.826 | 1.01E−07 | 0.868 | 0.946-0.790 | 1.14E−03 |
| hsa-miR-1304 | 0.853 | 0.891-0.814 | 2.31E−07 | 0.734 | 0.835-0.633 | 3.84E−02 |
| hsa-miR-1257 | 0.841 | 0.881-0.800 | 5.78E−07 | 0.725 | 0.827-0.623 | 4.72E−02 |
| hsa-miR-4639-5p | 0.839 | 0.880-0.799 | 6.49E−07 | 0.829 | 0.915-0.742 | 3.72E−03 |
| hsa-miR-33a* | 0.829 | 0.871-0.787 | 1.36E−06 | 0.835 | 0.920-0.749 | 3.12E−03 |
| hsa-miR-3714 | 0.824 | 0.867-0.781 | 2.01E−06 | 0.644 | 0.752-0.536 | 2.04E−01 |
| has-miR-let-7e | 0.813 | 0.857-0.769 | 4.52E−06 | 0.850 | 0.932-0.767 | 2.00E−03 |
| Has-miR-3133 | 0.809 | 0.853-0.764 | 5.89E−06 | 0.700 | 0.804-0.595 | 7.78E−02 |
| has-miR-1181 | 0.790 | 0.836-0.743 | 2.16E−05 | 0.647 | 0.755-0.540 | 1.93E−01 |
| has-miR-429 | 0.773 | 0.822-0.725 | 6.05E−05 | 0.805 | 0.897-0.714 | 6.99E−03 |
| has-miR-761 | 0.718 | 0.772-0.664 | 1.40E−03 | 0.738 | 0.839-0.638 | 3.55E−02 |
| has-miR-29a | 0.712 | 0.766-0.657 | 1.91E−03 | 0.799 | 0.891-0.706 | 8.37E−03 |
| has-miR-4714-5p | 0.693 | 0.749-0.637 | 4.76E−03 | 0.749 | 0.853-0.644 | 3.58E−02 |
| has-miR-let-7c | 0.601 | 0.663-0.538 | 1.40E−01 | 0.842 | 0.926-0.758 | 2.52E−03 |

The invention claimed is:

1. A method for detecting a miRNA biomarker in a test sample from a human subject at risk of developing pancreatic cancer or intraductal papillary mucinous neoplasm of the pancreas (IPMN), the method comprising:
   (a) contacting the test sample with a primer specific to the miRNA biomarker, wherein the miRNA biomarker comprises hsa-miR-33a*;
   (b) amplifying the hsa-miR-33a* biomarker to produce an amplification product in the test sample; and
   (c) measuring the hsa-miR-33a* expression level by determining the level of the amplification product in the test sample.

2. The method according to claim 1, wherein the method further comprises amplifying and measuring the expression level of at least one additional miRNA biomarker selected from hsa-let-7c, hsa-let-7e, hsa-let-7f, hsa-miR-103a, hsa-miR-1257, hsa-miR-1304, hsa-miR-151a-5p, hsa-miR-151b, hsa-miR-155, hsa-miR-16, hsa-miR-181, hsa-miR-181a, hsa-miR-181b, hsa-miR-192, hsa-miR-21, hsa-miR-221, hsa-miR-23a, hsa-miR-29a, hsa-miR-3120-3p, hsa-miR-3133, hsa-miR-3145-3p, hsa-miR-320a, hsa-miR-3692, hsa-miR-3714, hsa-miR-4256, hsa-miR-429, hsa-miR-4313, hsa-miR-4468, hsa-miR-4639-5p, hsa-miR-4642, hsa-miR-4666-3p, hsa-miR-4713-5p, hsa-miR-4714-5p, hsa-miR-4723-5p, hsa-miR-4770, hsa-miR-4801, hsa-miR-548d-3p, hsa-miR-616*, hsa-miR-761, and hsa-miR-93.

3. The method according to claim 1, wherein the method comprises amplifying and measuring the expression level of a group of at least two miRNA biomarkers, wherein the group of the at least two miRNA biomarkers is selected from: hsa-miR-33a* and hsa-miR-320a; hsa-miR-33a*, hsa-miR-16 and hsa-miR-320a; hsa-miR-33a*, hsa-miR-320a and hsa-miR-181; hsa-miR-33a*, hsa-miR-320a and hsa-miR-155; hsa-miR-33a*, hsa-miR-320a and hsa-miR-151b; hsa-miR-33a*, hsa-miR-320a and hsa-let7e; hsa-miR-33a*, hsa-miR-320a and hsa-miR-23a; hsa-miR-33a*, hsa-miR-320a and hsa-miR-151a; hsa-miR-33a*, hsa-miR-21 and hsa-let7e; hsa-miR-33a*, hsa-miR-23a and hsa-miR-21; and hsa-miR-33a*, hsa-miR-93 and hsa-miR-320a.

4. The method according to claim 1, wherein pancreatic cancer is pancreatic ductal adenocarcinoma.

5. The method according to claim 1, wherein the test sample comprises a biological sample selected from the group consisting of a tumor sample, a plasma sample, a blood sample, a cerebrospinal fluid (CSF) sample, or a serum sample.

6. The method according to claim 1, wherein the subject has not previously been diagnosed with pancreatic cancer or IPMN.

7. The method according to claim 1, wherein the subject has previously been diagnosed with pancreatic cancer or IPMN.

8. The method of claim 1, wherein contacting the test sample with the primer produces a primer-ligated hsa-miR-33a* biomarker, and wherein the amplifying step comprises amplifying a cDNA produced by reverse transcribing the primer-ligated hsa-miR-33a* biomarker.

9. The method of claim 8, wherein the hsa-miR33a* expression level is measured by transcribing the amplified cDNA to produce a sense target RNA, and detecting the sense target RNA by contacting the sense target RNA with an antisense probe.

10. A method for treating a human subject having pancreatic cancer or intraductal papillary mucinous neoplasm of the pancreas (IPMN), the method comprising administering to the human subject a therapy for pancreatic cancer or IPMN, wherein a test sample from the human subject has been determined to have an elevated expression level of miRNA biomarker hsa-miR-33a* as compared to a control sample, and wherein said therapy for pancreatic cancer or IPMN comprises surgery.

11. The method according to claim 10, wherein the expression level of a group of at least two miRNA biomarkers has been measured in the test sample, wherein the group of the at least two miRNA biomarkers are selected from: hsa-miR-33a* and hsa-miR-320a; hsa-miR-33a*, hsa-miR-16 and hsa-miR-320a; hsa-miR-33a*, hsa-miR-320a and hsa-miR-181; hsa-miR-33a*, hsa-miR-320a and hsa-miR-155; hsa-miR-33a*, hsa-miR-320a and hsa-miR-151b; hsa-miR-33a*, hsa-miR-320a and hsa-let7e; hsa-miR-33a*, hsa-miR-320a and hsa-miR-23a; hsa-miR-33a*, hsa-miR-320a and hsa-miR-151a; hsa-miR-33a*, hsa-miR-21 and hsa-let7e; hsa-miR-33a*, hsa-miR-23a and hsa-miR-21; and hsa-miR-33a*, hsa-miR-93 and hsa-miR-320a.

12. The method according to claim 10, wherein the pancreatic cancer is pancreatic ductal adenocarcinoma.

13. The method according to claim 10, wherein the test sample comprises a biological sample selected from the group consisting of a tumor sample, a plasma sample, a blood sample, a cerebrospinal fluid (CSF) sample, or a serum sample.

14. A method for treating a human subject having pancreatic cancer or intraductal papillary mucinous neoplasm of the pancreas (IPMN), the method comprising administering to the human subject a therapy for pancreatic cancer or IPMN, wherein a test sample from the human subject has been determined to have an elevated expression level of miRNA biomarker hsa-miR-33a* as compared to a control sample, and wherein said therapy for pancreatic cancer or IPMN comprises chemotherapy.

15. The method according to claim 14, wherein the expression level of a group of at least two miRNA biomarkers has been measured in the test sample, wherein the group of the at least two miRNA biomarkers is selected from: hsa-miR-33a* and hsa-miR-320a; hsa-miR-33a*, hsa-miR-16 and hsa-miR-320a; hsa-miR-33a*, hsa-miR-320a and hsa-miR-181; hsa-miR-33a*, hsa-miR-320a and hsa-miR-155; hsa-miR-33a*, hsa-miR-320a and hsa-miR-151b; hsa-miR-33a*, hsa-miR-320a and hsa-let7e; hsa-miR-33a*, hsa-miR-320a and hsa-miR-23a; hsa-miR-33a*, hsa-miR-320a and hsa-miR-151a; hsa-miR-33a*, hsa-miR-21 and hsa-let7e; hsa-miR-33a*, hsa-miR-23a and hsa-miR-21; and hsa-miR-33a* and hsa-miR-93 and hsa-miR-320a.

16. The method according to claim 14, wherein the pancreatic cancer is pancreatic ductal adenocarcinoma.

17. The method according to claim 14, wherein the test sample comprises a biological sample selected from the group consisting of a tumor sample, a plasma sample, a blood sample, a cerebrospinal fluid (CSF) sample, or a serum sample.

18. A method for treating a human subject having pancreatic cancer or intraductal papillary mucinous neoplasm of the pancreas (IPMN), the method comprising administering to the human subject a therapy for pancreatic cancer or IPMN, wherein a test sample from the human subject has been determined to have an elevated expression level of miRNA biomarker hsa-miR-33a* as compared to a control sample, and wherein said therapy for pancreatic cancer or IPMN comprises radiation.

19. The method according to claim 18, wherein the expression level of a group of at least two miRNA biomarkers has been measured in the test sample, wherein the group of at least two miRNA biomarkers is selected from: hsa-miR-33a* and hsa-miR-320a; hsa-miR-33a*, hsa-miR-16 and hsa-miR-320a; hsa-miR-33a*, hsa-miR-320a and hsa-miR-181; hsa-miR-33a*, hsa-miR-320a and hsa-miR-155; hsa-miR-33a*, hsa-miR-320a and hsa-miR-151b; hsa-miR-33a*, hsa-miR-320a and hsa-let7e; hsa-miR-33a*, hsa-miR-320a and hsa-miR-23a; hsa-miR-33a*, hsa-miR-320a and hsa-miR-151a; hsa-miR-33a*, hsa-miR-21 and hsa-let7e; hsa-miR-33a*, hsa-miR-23a and hsa-miR-21; and hsa-miR-33a*, hsa-miR-93 and hsa-miR-320a.

20. The method according to claim 18, wherein the pancreatic cancer is pancreatic ductal adenocarcinoma.

21. The method according to claim 18, wherein the test sample comprises a biological sample selected from the group consisting of a tumor sample, a plasma sample, a blood sample, a cerebrospinal fluid (CSF) sample, or a serum sample.

* * * * *